(12) United States Patent
Hanson et al.

(10) Patent No.: US 12,201,453 B2
(45) Date of Patent: Jan. 21, 2025

(54) MICRONEEDLE FABRICATION AND DEVICE IMPLANTATION

(71) Applicant: The Regents of the University of California, Oakland, CA (US)

(72) Inventors: Timothy L. Hanson, San Francisco, CA (US); Philip N. Sabes, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/392,987

(22) Filed: Dec. 21, 2023

(65) Prior Publication Data

US 2024/0237948 A1    Jul. 18, 2024

Related U.S. Application Data

(63) Continuation of application No. 16/463,323, filed as application No. PCT/US2017/063492 on Nov. 28, 2017, now Pat. No. 11,857,343.
(Continued)

(51) Int. Cl.
*A61B 5/00*     (2006.01)
*A61B 5/1459*   (2006.01)
(Continued)

(52) U.S. Cl.
CPC ............ *A61B 5/685* (2013.01); *A61B 5/1459* (2013.01); *A61B 5/1473* (2013.01); *A61B 5/6868* (2013.01); *A61K 41/0028* (2013.01); *A61N 1/0502* (2013.01); *A61N 1/0529* (2013.01); *A61N 1/0551* (2013.01); *A61N 5/0601* (2013.01); *B21F 45/008* (2013.01);
(Continued)

(58) Field of Classification Search
None
See application file for complete search history.

(56) References Cited

U.S. PATENT DOCUMENTS 3,987,839 A    10/1976  Pace
6,175,752 B1    1/2001  Say et al.
(Continued)

FOREIGN PATENT DOCUMENTS

WO    WO 2016/126340    11/2016

*Primary Examiner* — Roberts P Culbert
(74) *Attorney, Agent, or Firm* — Edward J. Baba; Bozicevic, Field & Francis LLP

(57) ABSTRACT

Methods are provided for the fabrication of microneedles. Microneedles fabricated according to the herein described methods will generally be constructed of multiple lengths of wire winded together, brazed and further manipulated to include a reversible engagement feature. The subject microneedles may find use in a variety of applications and, among other purposes, the reversible engagement feature of such a microneedle may by employed in implanting an implantable device into a biological tissue. Also provided are methods of inserting an implantable device into a biological tissue having an outer membrane. The subject methods may include ablating a section of the outer membrane and inserting the implantable device through the ablated section of outer membrane, including e.g., where the implantable device is inserted using a microneedle including e.g., those microneedles for which methods of fabrication are provided herein.

20 Claims, 11 Drawing Sheets

Related U.S. Application Data

(60) Provisional application No. 62/428,352, filed on Nov. 30, 2016.

(51) Int. Cl.
*A61B 5/1473* (2006.01)
*A61K 41/00* (2020.01)
*A61N 1/05* (2006.01)
*A61N 5/06* (2006.01)
*B21F 45/00* (2006.01)
B23K 1/00 (2006.01)
B23K 101/32 (2006.01)

(52) U.S. Cl.
CPC ............... *A61B 2562/12* (2013.01); *A61N 2005/0612* (2013.01); *A61N 2005/0651* (2013.01); *B23K 1/0008* (2013.01); *B23K 2101/32* (2018.08)

(56) References Cited

U.S. PATENT DOCUMENTS

| | | |
|---|---|---|
| 6,658,302 B1 | 12/2003 | Kuzma et al. |
| 8,202,280 B2 | 6/2012 | Richter |
| 2009/0277934 A1 | 11/2009 | Youngman |
| 2013/0267844 A1 | 10/2013 | McGuckin et al. |
| 2014/0046246 A1* | 2/2014 | Ferreira De Sa ..... A61M 37/00 604/22 |
| 2015/0080709 A1* | 3/2015 | Chaturvedi ........ A61B 17/3205 606/129 |
| 2017/0007813 A1 | 1/2017 | Negi et al. |

\* cited by examiner

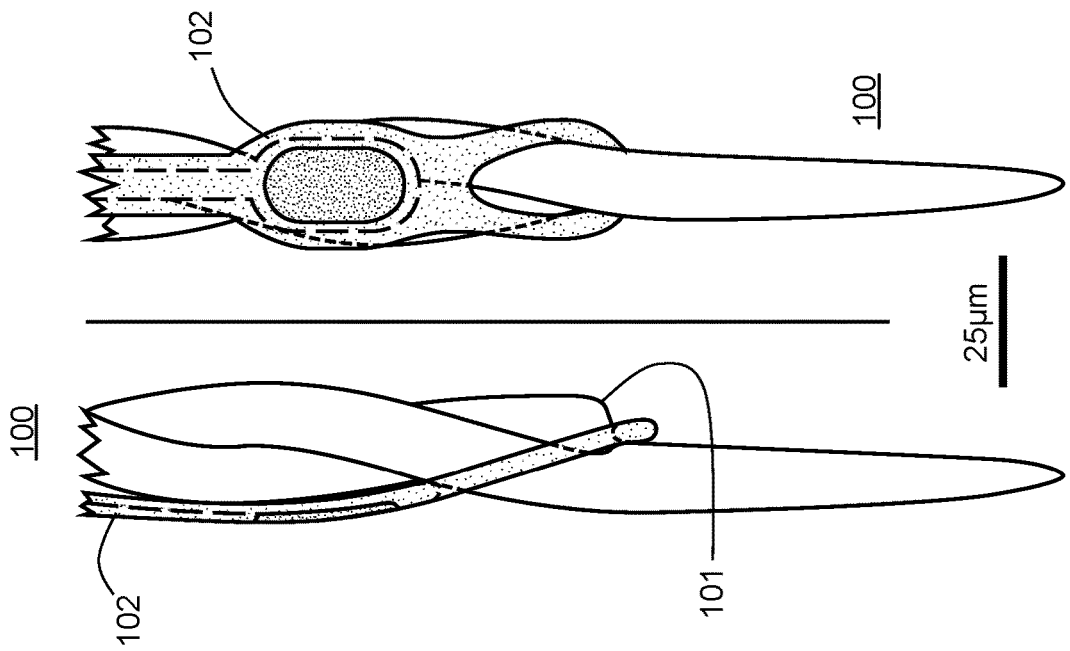

MICRONEEDLE FABRICATION AND DEVICE IMPLANTATION

CROSS-REFERENCE

This application is a continuation of U.S. application Ser. No. 16/463,323 filed May 22, 2019, issued as U.S. Pat. No. 11,857,343, which is a 371 of PCT/US2017/063492 filed Nov. 28, 2017, which claims priority to U.S. Application No. 62/428,352 filed Nov. 30, 2016, which are incorporated herein by reference.

STATEMENT REGARDING FEDERALLY SPONSORED RESEARCH

This invention was made with government support under Grant No. W911NF-15-2-0054 awarded by the Defense Advanced Research Projects Agency. The government has certain rights in the invention.

INTRODUCTION

The expansion of new microsurgical and neurosurgical techniques has driven forward the boundaries of many areas of research. For example, advanced neurosurgical techniques have advanced our understanding of neuronal function and the pathophysiologic dysfunction in various neurological disorders of numerous areas of the brain including subcortical structures. Additionally, advanced stereotaxic targeting techniques allow for specific targeting of both neural and non-neural structures with exquisite accuracy and precision.

Such improvements in surgical and targeting methodologies continue to drive the development of increasingly sophisticated tools which allow investigators to utilize these advances to their full extent. In neurobiology, for example, all of these factors combine to allow researchers access to neural circuits with high spatial and temporal resolution through the placement of implantable monitoring devices (e.g., electrodes) at many precise locations throughout the brain. Truly transformative neural activity mapping has been achieved through this approach.

The technology is neither optimal nor stationary, however, and thus continues to advance. Accordingly, improved methods of producing the ever shrinking tools that are employed in these methods stands to be greatly beneficial. In particular, fabrication of micro-scale instruments that are strong and have properties that increase ease of use and reliability continue to be of value. Such precision instruments also stand to benefit from improved methods of use, especially those that are designed with their physical limitations in mind while taking advantage of the desirable properties inherent in their small size.

SUMMARY

Methods are provided for the fabrication of microneedles. Microneedles fabricated according to the herein described methods will generally be constructed of multiple lengths of wire winded together, brazed and further manipulated to include a reversible engagement feature. The subject microneedles may find use in a variety of applications and, among other purposes, the reversible engagement feature of such a microneedle may by employed in implanting an implantable device into a biological tissue. Also provided are methods of inserting an implantable device into a biological tissue having an outer membrane. The subject methods may include ablating a section of the outer membrane and inserting the implantable device through the ablated section of outer membrane, including e.g., where the implantable device is inserted using a microneedle including e.g., those microneedles for which methods of fabrication are provided herein.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1 depicts a schematic side-view (left) and front-view (right) of a twisted-pair microneedle with implantable device electrode loaded. Braze is not shown.

FIG. 2 provides a photograph of a microneedle loaded into a cartridge, showing step and sharpened point at bottom.

DETAILED DESCRIPTION

Figure 3A:
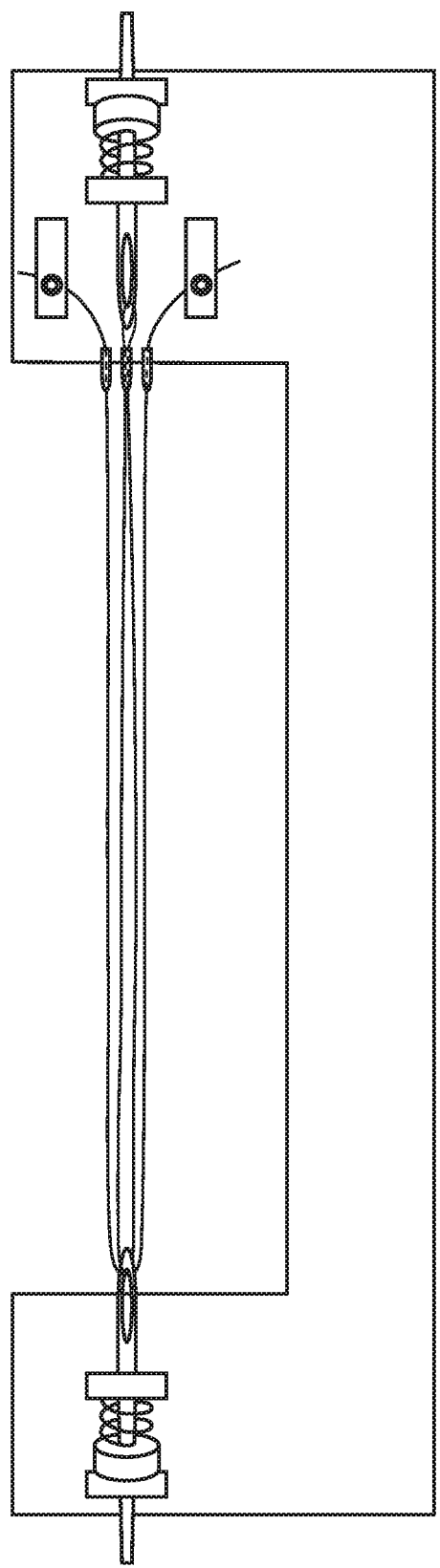
FIG. 3A-3D provide a schematic representation of a loaded needle fabrication jig and the sequence used in loading lengths of wire into a needle fabrication jig prior brazing according to embodiments of the present disclosure.

Methods are provided for the fabrication of microneedles. Microneedles fabricated according to the herein described methods will generally be constructed of multiple lengths of wire winded together, brazed and further manipulated to include a reversible engagement feature. The subject microneedles may find use in a variety of applications and, among other purposes, the reversible engagement feature of such a microneedle may by employed in implanting an implantable device into a biological tissue. Also provided are methods of inserting an implantable device into a biological tissue having an outer membrane. The subject methods may include ablating a section of the outer membrane and inserting the implantable device through the ablated section of outer membrane, including e.g., where the implantable device is inserted using a microneedle including e.g., those microneedles for which methods of fabrication are provided herein.

Before the present methods are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a wire" includes a plurality of such wires and reference to "the microneedle" includes reference to one or more microneedles and equivalents thereof, e.g. insertion needles, known to those skilled in the art, and so forth.

The publications discussed herein are provided solely for their disclosure prior to the filing date of the present disclosure. Nothing herein is to be construed as an admission that the present invention is not entitled to antedate such publication by virtue of prior invention. Further, the dates of publication provided may be different from the actual publication dates which may need to be independently confirmed.

Methods

As summarized above, embodiments of the present disclosure include those directed to methods of fabricating a microneedle. The fabricated microneedles, described in more detail below, may find use in a variety of applications, including but not limited to e.g., insertion into a biological tissue of interest, delivery of a cargo into a biological tissue, implantation of an implantable device into a biological tissue, and the like. Depending on the particular application, microneedles may thus be fabricated to have certain characteristics compatible with or desirable for their insertion into biological tissues. Such characteristics will vary and may include but are not limited to e.g., biocompatibility, rigidity, strength, minimal diameter, minimal displacement volume, and the like. Non-limiting examples of methods, systems, devices, etc., in which a microneedle fabricated as described herein may be employed include but are not limited to e.g., those described in PCT International Publication No. WO 2016/126340; the disclosure of which is incorporated herein by reference in its entirety.

The subject microneedles will generally be fabricated from multiple lengths of wire where two or more lengths of wire may be wound together. The actual number of lengths of wire wound together in fabricating a microneedle in the instant methods will vary and may range from 2 to 10 or more, including but not limited to e.g., 2 to 10, 2 to 8, 2 to 6, 2, 3, 4, 5, 6, 7, 8, 9, 10, etc. The lengths of wire used during fabrication may be different sections of the same continuous wire (e.g., looped) or may be sections of separate (i.e., individual) wires. It is noted that the individual lengths of wire from which the microneedles of the subject disclosure are fabricated will generally, but not necessarily, be unsuitable for use as a microneedle without one or more of the fabrication steps described herein. Put another way, the individual wires will generally, but not necessarily, have one or more characteristics that prevent their use alone as a microneedle as described herein, such as e.g., insufficient rigidity, insufficient strength, insufficient size, lack of certain desirable features (e.g., an engagement feature), etc.

In general, the subject methods of fabricating a microneedle will include winding multiple lengths of wire to from a helix, brazing the helix to generate a microneedle that includes the multiple lengths of wire, and further manipulating the lengths of wire of the brazed microneedle to produce desired features.

Wire Winding

As summarized above, the subject methods of fabricating a microneedle will generally include winding multiple lengths of wire together. For simplicity, in the following, wire winding will be most frequently described in relation to winding of two wires together; however, the instant methods are not so limited and an ordinary skilled artisan will readily understand that two lengths of wires or more than two lengths of wires may be employed. For example, as specifically set forth in the examples below, in some instances, four lengths of wire may be employed. Furthermore, as used herein the term "length of wire" may refer to a wire or a portion of a wire and, as such, a single wire may have multiple lengths or a length of wire may encompass an entire wire. As such, in the following, the term "length of wire" may be used interchangeably with "wire" for simplicity in some instances. An ordinary skilled artisan will readily understand that where two lengths of wire are described as being wound together the lengths may be portions of the same wire, i.e., looped back on itself, or may be present on separate wires.

Winding of wires of the subject methods may be performed under tension. Such winding under tension may generate a helix. In some instances, a helix of the subject disclosure may be referred to herein as a primary helix. The term "primary helix", as used herein, generally refers to a helix of wound wires wherein one of the wires of the helix functions as the point of the microneedle after fabrication. A wire of the primary helix may also be utilized to form an engagement feature of a microneedle. Tension may be applied to the wires using any suitable method including e.g., mounting the wires in a spring loaded apparatus configured to tension the wires during winding of a helix, e.g., a primary helix. Suitable apparatus for winding wires under tension include e.g., a winding jig having one or more springs configured to tension the wires. In some instances, a winding jig having two springs positioned on at each end of the sections of wire may be employed, such as but not limited to e.g., an exemplary winding jig as described herein. Where more than two wires are employed the additional wire(s) may be integrated into the primary helix (e.g., forming a three-stranded helix, a four-stranded helix, etc.) or may form a separate helix (e.g., around the primary helix, including e.g., those helices referred to herein as secondary helices).

Wire made of any suitable and appropriate material may be employed in the subject methods. Suitable and appropriate wire materials will include those materials that are sufficiently rigid and strong. In some embodiments, suitable wire is made of a rigid material, such as tungsten or an alloy thereof, and therefore the generated microneedle is correspondingly rigid (stiff). Convenient stiff, strong materials may include those having a relatively high Young's modulus. Additional suitable materials include, but are not limited to: tungsten carbide, iridium, tungsten-rhenium alloy, carbon fiber, boron, boride (e.g., BN), ceramic oxides and nitrides, and composite materials. In some embodiments, a suitable material may be alloyed with hafnium carbide (HfC) or zirconium carbide (ZrC) for additional stiffness. For example, in some instances, a wire material employed may be tungsten or an alloy thereof, e.g., tungsten-rhenium, including those alloyed with HfC or ZrC.

As noted above, suitable wire materials may also include carbon based materials and thus wires of the present fabrication methods may include one or more carbonaceous solids or carbonaceous materials. Suitable carbonaceous materials will vary and may include but are not limited to e.g., carbon fiber, carbon nanotube, etc.

Wires utilized in the subject methods may have a wide range of dimensions and thus a microneedle produced from the wound wires may correspondingly have a large variety of dimensions and geometries. Wires utilized in the instant fabrication methods may range in diameter from 4 µm or less to 100 µm or more, including but not limited to e.g., from 4 µm to 100 µm, from 4 µm to 50 µm, from 4 µm to 40 µm, from 4 µm to 30 µm, from 4 µm to 25 µm, from 4 µm to 20 µm, from 4 µm to 15 µm, from 4 µm to 10 µm, from 5 µm to 100 µm, from 5 µm to 50 µm, from 5 µm to 40 µm, from 5 µm to 30 µm, from 5 µm to 25 µm, from 5 µm to 20 µm, from 5 µm to 15 µm, from 5 µm to 10 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, etc. In some instances, the diameters of the wires employed in fabrication, whether the same or different, will be less than 100 µm, including e.g., less than 75 µm, less than 50 µm, etc.

The diameter of wound wires may essentially be the sum of the diameters of the individually wound wires. In some instances, the produced microneedle may be described according to its "maximum diameter". As used below, the term "maximum diameter" is used in the following context to mean the diameter of the microneedle at the point along its length (of the portion of the microneedle that is inserted or is to be inserted in a biological tissue) at which it is its widest. For example, in some cases, the microneedle has one diameter at the point of contact with the biological tissue, but another length farther up the microneedle (e.g., due to a change in geometry of the microneedle), and the 'maximum diameter' describes the diameter when the microneedle is its widest (along the portion of the microneedle that is inserted or is to be inserted). Likewise, the term "maximum cross sectional area" is used to mean the cross sectional area of the microneedle at the point along its length (of the portion of the microneedle that is inserted or is to be inserted in a biological tissue) at which it is its biggest (i.e., the 'maximum cross sectional area' describes the cross-sectional area when the microneedle is its widest, along the portion of the microneedle that is inserted or is to be inserted).

In some cases, the fabricated microneedle has a maximum diameter (e.g., along the length of insertion) of 80 µm or less (e.g., 70 µm or less, 65 µm or less, 60 µm or less, 55 µm or less, 50 µm or less, 55 µm or less, 50 µm or less, 45 µm or less, 40 µm or less, 35 µm or less, 30 µm or less, or 25 µm or less). For example, in some cases, the microneedle has a maximum diameter (e.g., along the length of insertion) of 65 µm or less. In some cases, the microneedle has a maximum diameter (e.g., along the length of insertion) of 35 µm or less.

In some cases, the fabricated microneedle has a maximum diameter (e.g., along the length of insertion) in a range of from 10 to 80 µm (e.g., from 10 to 70 µm, from 10 to 65 µm, from 10 to 60 µm, from 10 to 55 µm, from 10 to 50 µm, from 10 to 45 µm, from 10 to 40 µm, from 10 to 35 µm, from 15 to 80 µm, from 15 to 70 µm, from 15 to 65 µm, from 15 to 60 µm, from 15 to 55 µm, from 15 to 50 µm, from 15 to 45 µm, from 15 to 40 µm, from 15 to 35 µm, from 20 to 80 µm from 20 to 70 µm, from 20 to 65 µm, from 20 to 60 µm, from 20 to 55 µm, from 20 to 50 µm, from 20 to 45 µm, from 20 to 40 µm, from 20 to 35 µm, from 25 to 80 µm from 25 to 70 µm, from 25 to 65 µm, from 25 to 60 µm, from 25 to 55 µm, from 25 to 50 µm, from 25 to 45 µm, from 25 to 40 µm, or from 25 to 35 µm). In some cases, the microneedle has a maximum diameter (e.g., along the length of insertion) in a range of from 20 to 65 µm. In some cases, the microneedle has a maximum diameter (e.g., along the length of insertion) in a range of from 25 to 65 µm. In some cases, the microneedle has a maximum diameter (e.g., along the length of insertion) in a range of from 20 to 35 µm. In some cases, the microneedle has a maximum diameter (e.g., along the length of insertion) in a range of from 25 to 35 µm.

In some cases, the fabricated microneedle has a maximum cross sectional area (e.g., along the length of insertion) of 5000 $µm^2$ or less (e.g., 4500 $µm^2$ or less, 4000 $µm^2$ or less, 3500 $µm^2$ or less, 3000 $µm^2$ or less, 2500 $µm^2$ or less, 2000 $µm^2$ or less, 1500 $µm^2$ or less, 1000 $µm^2$ or less, 800 $µm^2$ or less, 750 $µm^2$ or less, or 700 $µm^2$ or less). In some cases, the microneedle has a maximum cross sectional area (e.g., along the length of insertion) of 4000 $µm^2$ or less (e.g., 3500 $µm^2$ or less, 3000 $µm^2$ or less, 2500 $µm^2$ or less, 2000 $µm^2$ or less, 1500 $µm^2$ or less, 1000 $µm^2$ or less, 800 $µm^2$ or less, 750 $µm^2$ or less, or 700 $µm^2$ or less). In some cases, the microneedle has a maximum cross sectional area (e.g., along the length of insertion) of 3500 μm² or less (e.g., 3000 μm² or less, 2500 μm² or less, 2000 μm² or less, 1500 μm² or less, 1000 μm² or less, 800 μm² or less, 750 μm² or less, or 700 μm² or less). In some cases, the microneedle has a maximum cross sectional area (e.g., along the length of insertion) of 2000 μm² or less (e.g., 1500 μm² or less, 1000 μm² or less, 800 μm² or less, 750 μm² or less, or 700 μm² or less). In some cases, the microneedle has a maximum cross sectional area (e.g., along the length of insertion) of 1000 μm² or less (e.g., 800 μm² or less, 750 μm² or less, or 700 μm² or less).

In some cases, the fabricated microneedle has a maximum cross sectional area (e.g., along the length of insertion) in a range of from 250 to 4000 μm² (e.g., from 250 to 3500 μm², from 250 to 3000 μm², from 250 to 2500 μm², from 250 to 3000 μm², from 250 to 2500 μm², from 250 to 2000 μm², from 250 to 1500 μm², from 250 to 1000 μm², from 250 to 800 μm², from 400 to 4000 μm², from 400 to 3500 μm², from 400 to 3000 μm², from 400 to 2500 μm², from 400 to 3000 μm², from 400 to 2500 μm², from 400 to 2000 μm², from 400 to 1500 μm², from 400 to 1000 μm², from 400 to 800 μm², from 500 to 4000 μm², from 500 to 3500 μm², from 500 to 3000 μm², from 500 to 2500 μm², from 500 to 3000 μm², from 500 to 2500 μm², from 500 to 2000 μm², from 500 to 1500 μm², from 500 to 1000 μm², from 500 to 800 μm², from 1000 to 4000 μm², from 1000 to 3500 μm², from 1000 to 3000 μm², from 1000 to 2500 μm², from 1000 to 3000 μm², from 1000 to 2500 μm², from 1000 to 2000 μm², from 1000 to 1500 μm², from 2000 to 4000 μm², from 2000 to 3500 μm², from 2000 to 3000 μm², from 2000 to 2500 μm², from 2000 to 3000 μm², from 2000 to 2500 μm², from 2500 to 4000 μm², from 2500 to 3500 μm², from 2500 to 3000 μm², from 2500 to 2500 μm², or from 2500 to 3000 μm²).

In some cases, the fabricated microneedle has a maximum cross sectional area (e.g., along the length of insertion) in a range of from 2000 to 4500 μm². In some cases, the microneedle has a maximum cross sectional area (e.g., along the length of insertion) in a range of from 2500 to 4000 μm². In some cases, the microneedle has a maximum cross sectional area (e.g., along the length of insertion) in a range of from 500 to 1000 μm².

In some instances, four or more wires may be wound into two or more helices, including e.g., an inner primary helix and an outer secondary helix. Where wires are wound into two or more helices the two or more helices may be wound one at a time or simultaneously. For example, in some instances, multiple lengths of wire may be loaded into a wire winding jig such that winding the wires simultaneously forms a primary helix, that includes wires that will eventually form the microneedle point and the engagement feature, and a secondary helix, that includes one or more additional wires. Secondary helices, as described herein, may serve to strengthen the final fabricated microneedle and/or add additionally desired diameter to the microneedle.

Brazing

As summarized above, the subject methods of fabricating a microneedle will generally include brazing the wound wire. Brazing is a metal-joining process whereby filler metal (i.e., brazing material) is heated above its melting point and distributed between two or more close-fitting parts by capillary action. Generally, the brazing material is brought slightly above its melting (i.e., liquidus) temperature and is then applied to the base metal (i.e., the metal to be joined) where it flows over the base metal (also referred to as wetting). The wetted base metal is then cooled to join the pieces together. In some instances, brazing may be performed using a flux to prevent oxides from forming when the metal is heated. In some instances, brazing may be performed under a suitable atmosphere including e.g., an inert or reducing atmosphere, to prevent oxidation. In some instances, e.g., when brazing is performed under a suitable environment, brazing may be performed in the absence of flux.

Accordingly, the instant methods may include brazing the wound wire to join the individual lengths of wire together. The brazing material utilized may vary depending on a variety of factors, including e.g., the wires to be joined or the application method. For example, in some instances, the wound wire may be a carbonaceous wire and carbide forming elements may be employed in the braze alloy, such as but not limited to e.g., nickel, chromium, iron, etc. In some instances, e.g., where tungsten wire is used, a group 11 base alloy may be employed such e.g., copper, silver, gold, etc. Furthermore, alloys of group 11 metals may also find use in brazing employed in the subject methods including but not limited to e.g., iridium alloys of group 11 metals including but not limited to e.g., copper-iridium alloy, gold-iridium alloy, sliver-iridium alloy, and the like. In some instances, the brazing material may include an alloy containing iridium, an alloy containing scandium, an alloy containing zirconium, an alloy containing nickel, an alloy containing silicon, an alloy containing beryllium, and the like.

Brazing may be performed in a brazing machine, including e.g., those machines specifically designed for brazing wound wires. Useful brazing machines will vary and will generally include an apparatus for holding the wound wire and a crucible (also referred to in some instances as a heater basket) to contain the brazing material at a temperature sufficient for brazing. Accordingly, in methods of fabrication of the present disclosure a wound wire, e.g., held in a wire winding jig or other apparatus for holding the wound wire, may be contacted with the brazing material in the crucible, e.g., by raising the crucible and/or lowering the wound wire to make contact.

In some instances, a brazing machine may include an apparatus for oscillating the wound wire through the brazing material. As such, in some instances, the wound wire, e.g., a primary helix, a secondary helix or both, is oscillated laterally (i.e., back-and-forth) through the braze material. Accordingly, the movement of the wire may be lateral movement relative to the braze material and/or crucible to facilitate wetting a length of wound wire that exceeds the diameter of the crucible. Such oscillating may be achieved through any convenient mechanism including but not limited to e.g., one or more pulleys present on the brazing machine and configured to oscillate the wound wire laterally. The rate at which wound wire is oscillated through the brazing material may also vary and may range from 0.01 cm/s or less to 100 cm/s or more including but not limited to e.g., 0.01 cm/s to 100 cm/s, 0.1 cm/s to 100 cm/s, 0.01 cm/s to 10 cm/s, 0.1 cm/s to 10 cm/s, 0.1 cm/s to 5 cm/s, 0.5 cm/s to 10 cm/s, 0.5 cm/s to 5 cm/s, 0.5 cm/s to 2 cm/s, 0.5 cm/s, 1 cm/s, 1.5 cm/s, 2 cm/s, etc.

Crucibles useful in methods of fabrication as described herein will also vary depending on various factors including e.g., the brazing material employed. For example, methods of heating the crucible may vary and may include but are not limited to e.g., electrical/resistance heating, laser heating, and the like. In some instances, the crucible may be electrically heated and an associated brazing machine may include one or more heavy current busses connected to the crucible. Crucibles of the subject methods may be made of a variety of materials including but not limited to e.g., tungsten and tungsten alloy materials, carbonaceous materials, and the like. In some instances, an employed crucible is made of boron-nitride.

A brazing machine may further include an enclosed chamber. Such chambers find use in controlling the brazing atmosphere including but not limited to controlling the atmospheric pressure during brazing, controlling the atmospheric composition during brazing (e.g., gas composition, moisture, etc.). Accordingly, useful chambers include vacuum chambers and chambers that include a vacuum feed-through. In some instances, brazing is performed under a vacuum including but not limited to e.g., a vacuum of less than 760 m Torr, including but not limited to e.g., less than 750 m Torr, less than 500 mTorr, from 250 mTorr to 750 m Torr, from 400 mTorr to 750 mTorr, from 500 m Torr to 600 m Torr, and the like. In some instances, the brazing chamber may be kept very dry and brazing may be performed under low moisture conditions including e.g., where the pressure ratio of hydrogen to water is sufficiently high to reduce any surface oxides on the most oxidizable surfaces (e.g., tungsten surfaces) at the maximum process temperature. In some instances, brazing under low moisture conditions includes flowing a shielding gas through the brazing chamber. Useful shielding gases will vary and may include but are not limited to e.g., a mixture of hydrogen and argon including e.g., a 20% hydrogen mixture with argon. In some instances, prior to flowing a shielding gas through the brazing chamber the chamber is subjected to a vacuum of less than 100 m Torr, including but not limited to e.g., less than 50 mTorr, less than 10 mTorr, less than 5 m Torr, etc.

Vacuum conditions and/or the presence of a shielding gas may not be limited to brazing steps and may, in some instances, be present before or after brazing. For example, in some instances, a vacuum may be applied prior to brazing including e.g., during one or more steps that precedes brazing, including e.g., during wire winding. In some instances, a vacuum may be applied following brazing including e.g., during one or more steps that follows brazing, including e.g., during further manipulating the brazed microneedle (e.g., fatiguing, sharpening, etc.).

In some instances, the wound wire may be heated during brazing. Useful methods of heating the wound wire during brazing will vary and may include but not limited to e.g., electrical/resistance heating, laser heating, and the like. In some embodiments, the brazing chamber and/or the apparatus for holding the wound wire during brazing may include an electrical connection for passing current through the wound wire to heat the wire during brazing. In some instances, the wound wire may be not subjected to additional heating (i.e., heating in addition to that imparted by the molten brazing material) through, e.g., electrical or laser heating, during brazing.

In some instances, brazing of the wound wire may include the application of a base solvent material that is not incorporated into the brazed wire. In some instances, a base solvent material may be used to dissolve a braze material and allow the braze material to alloy with the wire material (e.g., W, W—Re, etc.). Useful solvent materials will vary and may include but not limited to e.g., copper, gold, etc. In such embodiments, the solvent material may be applied to the wire as a base and used to dissolve a braze material such as but not limited to e.g., nickel, chromium, iron, cobalt, etc. Following brazing, the wire may be heated, e.g., utilizing any convenient method (e.g., electrical/resistance, laser, etc.) to evaporate away the solvent base material while heating the brazing material sufficiently above the liquidus temperature to alloy directly with the wire material. In some embodiments, use of a brazing process involving a solvent base material may be employed to generate a stronger and/or stiffer joint than that achieved through brazing without the solvent material.

In some instances, the subject fabrication methods may include tempering the microneedle, e.g., tempering following brazing. Such tempering may include controlled heating and/or cooling of the microneedle. In some instances, the microneedle is tempered by heating the microneedle following brazing. Useful methods of heating the microneedle during or following brazing will vary and may include but are not limited to e.g., electrical/resistance heating, laser heating, and the like. Useful tempering temperatures will vary and may range from less than 100° C. to 1000° C. or more including but not limited to e.g., from 100° C. to 1000° C., from 200° ° C. to 1000° C., from 300° C. to 1000° C., from 400° C. to 1000° C., from 100° ° C. to 900° C., from 100° C. to 800° C., from 100° C. to 700° C., from 100° C. to 600° C., from 200° ° C. to 800° C., from 300° ° C. to 700° C., from 400° C. to 600° C., 500° C., etc. Useful tempering times will also vary and may range from minutes or less to hours or more, including but not limited to e.g., from 5 min. to 6 hours, from 10 min. to 3 hours, from 15 min. to 1 hour, about 30 min., about 1 hour, etc.

After brazing is complete the wires of the helix will be substantially joined by the brazing process forming a microneedle unit. The microneedle will generally, but need not necessarily, be subjected to further manipulation to apart certain desired characteristics and/or features upon the produced microneedle. Such manipulations may be applied to the microneedle as a whole or, although brazed, to individual wires of which the microneedle is made up.

Manipulations

As summarized above, the subject methods of fabricating a microneedle may include further manipulating one or more of the lengths of wire of the microneedle to produce one or more desired features or impart one or more desired characteristics upon the microneedle or a portion thereof. In some instances, further manipulation of the microneedle following brazing may be employed to produce a reversible engagement feature on the microneedle.

A microneedle fabricated according to the subject methods will generally include an engagement feature, e.g., as corresponding to an engagement feature present on an implantable device. Such engagement features will generally be "reversible" allowing the engagement of the feature, e.g., during implantation of a cargo, and disengagement of the feature, e.g., to leave the cargo implanted when removing the microneedle. For example, prior to and during implantation, an implantable device may be reversibly engaged with a microneedle (via the corresponding engagement features of the implantable device and the microneedle). Essentially, the microneedle, with device loaded, is inserted into a biological tissue (e.g., to a desired depth), and the microneedle is then retracted, thereby disengaging the implantable device from the microneedle and allowing the implantable device to remain implanted in the biological tissue at a desired position. Microneedles fabricated according to the herein described method may be employed individually (e.g., to insert one implantable device or multiple implantable devices) or in parallel with additional microneedles such that a plurality of implantable devices is implanted into the biological tissue using a plurality of microneedles.

The engagement features present on microneedles fabricated according to present methods will vary. As described above, in some instances, the fabrication method facilitates desirable fracturing of the microneedle to generate the engagement feature; however, the engagement feature need not necessarily be employed, e.g., to engage the engagement feature of an implantable device, as fractured and may, in some instances, be further shaped or modified as desired. Accordingly, essentially any desirable shape of engagement feature may be fashioned from an engagement feature generated through fracturing as described above.

In some embodiments, the engagement feature of the microneedle is positioned in a distal region of the microneedle. As used herein the "distal region" is the distal-most 25% of the microneedle (relative to the entire length of the microneedle). To be clear the distal end of the in microneedle is the tip of the needle that penetrates into the target tissue (e.g., the biological tissue).

In some cases, the engagement feature of the microneedle is positioned in the distal region of the microneedle, but not at the distal end (meaning, the engagement feature is set back from the distal tip, i.e., the engagement feature is set back from the distal end). For example, in some cases, the engagement feature of the microneedle is positioned in the distal region of the microneedle, but is not present in the distal most 10% of the distal region. In some cases, the engagement feature of the microneedle is positioned in the distal region of the microneedle, but is not present in the distal most 5% of the distal region. In some cases, the engagement feature of the microneedle is positioned in the distal region of the microneedle, but is not present in the distal most 3% of the distal region. In some cases, the engagement feature of the microneedle is positioned in the distal region of the microneedle, but is not present in the distal most 2% of the distal region. In some cases, the engagement feature of the microneedle is positioned in the distal region of the microneedle, but is not present in the distal most 1% of the distal region. In some cases, the engagement feature of the microneedle is positioned in the distal region of the microneedle, but is not present in the distal most 0.5% of the distal region.

In some cases, the engagement feature of the microneedle is positioned at least 5 µm away from the distal end of the microneedle (e.g., at least 10 µm, at least 15 µm, at least 20 µm, at least 25 µm, at least 30 µm, at least 35 µm, at least 40 µm, at least 45 µm, or at least 50 µm away from the distal end). In some cases, the engagement feature of the microneedle is positioned at least at least 10 µm away from the distal end of the microneedle (e.g., at least 15 µm, at least 20 µm, at least 25 µm, at least 30 µm, at least 35 µm, at least 40 µm, at least 45 µm, or at least 50 µm away from the distal end). In some cases, the engagement feature of the microneedle is positioned at least at least 20 µm away from the distal end of the microneedle (e.g., at least 25 µm, at least 30 µm, at least 35 µm, at least 40 µm, at least 45 µm, or at least 50 µm away from the distal end).

In some cases, the engagement feature of the microneedle is positioned in the distal region of the microneedle, but is positioned at least 5 µm away from the distal end (e.g., at least 10 µm, at least 15 µm, at least 20 µm, at least 25 µm, at least 30 µm, at least 35 µm, at least 40 µm, at least 45 µm, or at least 50 µm away from the distal end). In some cases, the engagement feature of the microneedle is positioned in the distal region of the microneedle, but is positioned at least 10 µm away from the distal end (e.g., at least 15 µm, at least 20 µm, at least 25 µm, at least 30 µm, at least 35 µm, at least 40 µm, at least 45 µm, or at least 50 µm away from the distal end). In some cases, the engagement feature of the microneedle is positioned in the distal region of the microneedle, but is positioned at least 20 µm away from the distal end (e.g., at least 15 µm, at least 20 µm, at least 25 µm, at least 30 µm, at least 35 µm, at least 40 µm, at least 45 µm, or at least 50 µm away from the distal end).

In some cases, the engagement feature of the microneedle is positioned within 100 µm of the distal end of the microneedle (e.g., within 90 µm, 80 µm, 70 µm, 60 µm, 50 µm, 40 µm, 30 µm, 20 µm, or 10 µm, of the distal end of the microneedle). In some cases, the engagement feature of the microneedle is positioned within 100 µm of the distal end of the microneedle (e.g., within 90 µm, 80 µm, 70 µm, 60 µm, 50 µm, 40 µm, 30 µm, 20 µm, or 10 µm, of the distal end of the microneedle), but is not positioned at the distal end of the microneedle. For example in some cases, the engagement feature of the microneedle is positioned within 100 µm of the distal end of the microneedle (e.g., within 90 µm, 80 µm, 70 µm, 60 µm, 50 µm, 40 µm, 30 µm, 20 µm, or 10 µm, of the distal end of the microneedle), and is positioned at least 5 µm away from the distal end (e.g., at least 10 µm, at least 15 µm, at least 20 µm, at least 25 µm, at least 30 µm, at least 35 µm, at least 40 µm, at least 45 µm, or at least 50 µm away from the distal end). In some cases, the engagement feature of the microneedle is positioned within 100 µm of the distal end of the microneedle (e.g., within 90 µm, 80 µm, 70 µm, 60 µm, 50 µm, 40 µm, 30 µm, 20 µm, or 10 µm, of the distal end of the microneedle), and is positioned at least 10 µm from the distal end of the microneedle. In some cases, the engagement feature of the microneedle is positioned within 100 µm of the distal end of the microneedle (e.g., within 90 µm, 80 µm, 70 µm, 60 µm, 50 µm, 40 µm, 30 µm, 20 µm, or 10 µm, of the distal end of the microneedle), and is positioned at least 20 µm from the distal end of the microneedle. In some cases, the engagement feature of the microneedle is positioned within 80 µm of the distal end of the microneedle (e.g., within 70 µm, 60 µm, 50 µm, 40 µm, 30 µm, 20 µm, or 10 µm, of the distal end of the microneedle), and is positioned at least 10 µm from the distal end of the microneedle. In some cases, the engagement feature of the microneedle is positioned within 80 µm of the distal end of the microneedle (e.g., within 70 µm, 60 µm, 50 µm, 40 µm, 30 µm, 20 µm, or 10 µm, of the distal end of the microneedle), and is positioned at least 20 µm from the distal end of the microneedle.

As noted above, the engagement feature may be produced through fracturing a wire of the multi-wire microneedle. Such fracturing may be achieved by fatiguing a distal end of the length of wire to cause the wire to fracture at or near a desired position, e.g., as described above. As described in detail above, desired positions for the engagement feature will generally be positioned at some distance from the distal trip of the microneedle. Accordingly, in the case of the multi-wire microneedles described herein, the engagement feature will generally be positioned along a second length of wire (e.g., a longer length of wire, an unfractured length of wire, or the like) that may serve as the distal tip of the microneedle. Methods or microneedle preparation, including those described, herein may be employed to induce the wire to facture at or near the desired point, e.g., through the mechanical influences imparted by the one or more fabrication steps (e.g., winding, brazing, tempering, etc.) or combinations thereof.

Fatiguing of wires to generate a fracture at a desired position, as noted above, is influenced by the fabrication steps used in generating the microneedle. Thus, following brazing one or more wires may be fatigued at the point where the wire leaves the brazed helix of which it is a component. Different wires may be fatigued to fracture at different points, e.g., a wire fatigued to produce an engagement feature may fracture at a point different from an additional wire utilized to provide support to the wires of the primary helix.

In some instances, a wire of the microneedle may be further manipulated by sharpening. For example, in some embodiments, the wire that forms the distal tip of the microneedle may be sharpened at its end. In some instance, e.g., where a microneedle has an introduced engagement feature, the end of the wire that is sharpened may be the end that is most proximal to the engagement feature. Any convenient method of sharpening the end of the wire or tip of the microneedle may be employed including but not limited to e.g., electrochemical etching.

Electrochemical etching techniques employed in the herein described methods will vary any may include but are not limited to e.g., those electrochemical etching techniques and/or etching baths suitable for generating a fine point, those electrochemical etching techniques and/or etching baths suitable for removing brazing material, and the like. In some instances, the method may include electrochemically etching the microneedle in $FeCl_3$. In some instances, the method may include electrochemically etching the microneedle in NaOH. Electrical current may or may not be employed during etching. In some instances, etching is performed in NaOH with current ranging from 0.5 V to 10 V (e.g., 1 V to 6 V).

As noted above, in various steps of the present methods, e.g., before, during or after brazing, the method may include passing electrical current through one or more lengths of wire. Current passing through the wire may be employed to serve for a variety of different purposes including but not limited to e.g., heating the wire to a desired temperature, re-nature the crystal structure of the wire, clean the surface of the wire, and the like. Exemplary instances where current may be employed to heat the wire(s), e.g., before, during or after brazing, have been described above. In some instances, at various steps throughout the fabrication method current passed through the wire(s) may be sufficient to raise the temperature of the primary helix, the secondary helix or both to at least 500° C., including but not limited to e.g., at least 600° C., at least 700° C., at least 800° C., at least 900° C., at least 1000° C., at least 1100° C., at least 1200° C., at least 1300° C., at least 1400° C., at least 1500° C., at least 1600° C., at least 1700° C., at least 1800° C., at least 1900° C., at least 2000° C., etc. Useful electrical currents include those sufficient to reach a desired temperature in a particular type of wire, including e.g., one or more of the particular types of wire described herein. For example, in some instances, a useful current may include a current sufficient to raise the temperature of the primary helix, the secondary helix or both to about 1300° C. for pure tungsten wire and the like. In some instances, a useful current may include a current sufficient to raise the temperature of the primary helix, the secondary helix or both to about 1600° C. for tungsten-rhenium wire and the like. Current may be applied directly to the wire(s) or may be applied indirectly, e.g., through one or more electrical connections present on an apparatus utilized during fabrication including but not limited to e.g., a winding jig, a brazing machine, and the like.

As noted above, passing current through the wire may serve to re-nature the wire including e.g., where the current is sufficient to recrystallize the lengths of wire. As-drawn many of the wires suitable for use in the subject fabrication methods have elongated crystalline domains, which leads to ductility and high tensile strength of the material. These characteristics of the wire may be manipulated, e.g., to render the crystalline domains more regular, through the application of stress (e.g., tension during winding) and/or heat/current through the wire to orient the domains more perpendicular to the direction of applied stress. Furthermore, due to reduced emission area and nonlinear dependence of resistance on temperature, the helical area of the wound wire can be brought to a temperature sufficient for recrystallization while the free ends of the helices are kept below the recrystallization temperature and do not recrystallize. Therefore, recrystallization may, in some instances, be limited to only the helically wound sections of wire while the free ends not incorporated into the helix are not recrystallized. Accordingly, in such circumstances, differences between the ductility and brittleness of the helical and free ends of the wire may be employed to induce fracturing at or near desired positions during fatiguing steps biasing the fracture point closer to the helix. Furthermore, the alignment of the crystal structure of the wire due to recrystallizing may also be employed to increase the frequency of desirable fracturing of the wire which generates engagement features.

During manipulations involving heating of the wire, microneedle and/or a helix thereof to a desired temperature, including e.g., a temperature sufficient for recrystallization, etc., the temperature of the wire, microneedle and/or a helix thereof may be monitored. Any suitable method of monitoring the temperature of the wire may be employed. For example, in some instances, the temperature of the wire may be estimated, e.g., by observing the color of the wire by a skilled observer.

In some instances, monitoring the temperature of the wire may include measuring the temperature of one or more lengths of the wire. Temperature monitoring may be employed using any convenient technique and may be performed during any step where or method by which the wires are heated. In some instances, the temperature of the wire may be measured while the current is passing through the wire. Useful methods of measuring the temperature of the wire that may be employed include but are not limited to e.g., an optical measurement (e.g., as performed using an optical pyrometer), an electrical measurement (e.g., as performed by measuring changes in resistance), and the like.

The manipulations described herein may be applied to any wire of a microneedle and, e.g., equally applied to wires of a primary helix or a secondary helix, when present, alike. For example, in some instances, while fatiguing may be employed to generate an engagement feature in one wire of a microneedle, fatiguing may be similarly employed to shorten the wire(s) of a secondary helix thus shaping the microneedle as desired. Further methods may be employed to shape and/or adjust the characteristics of fabricated microneedles as desired including but not limited to e.g., through the use of sandpaper or other abrasive.

Insertion Through a Membrane

As summarized above, the methods of the present disclosure include inserting an implantable device into a biological tissue having an outer membrane. Methods involving insertion of a device into a biological tissue having an outer membrane may include ablating a section of the outer membrane and inserting the device through the ablated section of outer membrane. Such methods may or may not include where the implantable device is inserted using a microneedle, including e.g., those fabricated according to the methods described herein.

The subject methods will generally be performed on a biological tissue. Such biological tissues include but are not limited to: brain, muscle, liver, pancreas, spleen, kidney, bladder, intestine, heart, stomach, skin, colon, and the like.

In some cases, the targeted biological tissue is a central nervous system (CNS) tissue, including but not limited to e.g., brain tissue, spinal cord tissue, eye tissue, and the like. The biological tissue can be from any multicellular organism including but not limited to invertebrates, vertebrates, fish, birds, mammals, rodents (e.g., mice, rats), ungulates, cows, sheep, pigs, horses, non-human primates, and humans. In some cases, the biological tissue is ex vivo (e.g., a tissue explant). In some cases, the biological tissue is in vivo (e.g., the method is a surgical procedure performed on a subject).

The subject methods allow for the insertion of an implantable device into a biological tissue having an outer membrane. As such, in some instances, the biological tissue upon which the method is employed may be a tissue having an outer membrane. Outer membranes of biological tissues may, in some instances, inhibit or otherwise negatively impact the insertion of the device. In some instances, biological tissues may not inhibit or otherwise negatively impact the insertion of the device but it may be nonetheless desirable to keep the membrane as intact as possible (e.g., to increase the likelihood of a successful procedure (e.g., to increase positive surgical outcomes and/or decrease the instances of negative surgical outcomes). Non-limiting examples of membranes that may be present on biological tissues include but are not limited to e.g., dura, pia-arachnoid complex, and the like.

Implantation through the outer membrane of the subject tissue may be achieved by ablating a section of the outer membrane. In some instances, such ablation may be referred to as "micro drilling" or "laser micro drilling" as the subject method, in some instances, is employed to induce one or more holes in the subject membrane through which the implantable device may be introduced but otherwise leave the membrane intact. The subject methods will generally include ablating the section of membrane through the use of a laser. In some instances, the laser employed may be a Q-switched laser.

Prior to applying the laser for ablation of membrane tissue, the membrane may be contacted with a photosensitizer. By "photosensitizer" as used herein is generally meant an agent that sensitizes the tissue to which it is applied to the laser as compared to tissue where the photosensitizer is not applied. Photosensitizers of the subject methods will generally have a particular wavelength that is strongly absorbed by the photosensitizer, referred to herein as a "wavelength of strong absorption". When subjected to light (e.g., laser light) corresponding to its wavelength of strong absorption the photosensitizer will disproportionately absorb energy from the light (e.g., laser light) as compared to other molecules. As such, cells and/or tissues contacted with the photosensitizer and subjected to light (e.g., laser light) corresponding the wavelength of strong absorption of the photosensitizer will disproportionately absorb energy from the light (e.g., laser light) leading to ablation of the cell and/or tissue.

Useful photosensitizers will vary and generally include those agents having a wavelength of strong absorption, such as e.g., many dyes. In some instances, depending on the application, photosensitizers employed may also be those that are biocompatible such that they do not adversely affect the tissue or cells to which they are applied in the absence of applied light (e.g., applied laser light) that corresponds to the wavelength of strong absorption. In some instances, a photosensitizer employed in the subject methods may be erythrosin B.

Ablation of the section of membrane according to the present methods may include applying a photosensitizer to the membrane and subjecting the applied photosensitizer to laser light having an emission wavelength that corresponds to the wavelength of strong absorption of the photosensitizer. The photosensitizer may be applied broadly to the membrane or to specific locations where ablation is desired. Given the general ability to shape a laser light beam as desired, e.g., through the use of optical components such as mirrors, lens, etc., the laser may be specifically applied to an area of the membrane where ablation is desired, regardless of whether the photosensitizer is applied broadly or to specific locations of the membrane. In some instances, the emission wavelength of the employed laser is a non-ionizing emission wavelength. In some instances, the laser employed is a green laser having a wavelength between about 495 nm to about 570 nm. In some instances the emission wavelength of the laser is 527 nm. In some instances, application of the laser to tissues to which the photosensitizer has not been applied does not result in ablation or otherwise damage or adversely affect the tissue.

Following ablation of the section of membrane an implantable device may be inserted through the hole in the membrane and into the biological tissue at any desired depth. In some instances, implantation of the implantable device may be facilitated through the use of a microneedle. For example, in some instances, a microneedle may be employed that includes an engagement feature corresponding to an engagement feature present on the implantable device and the engagement feature may allow implantation of the device and subsequent retraction of the microneedle. In some instances, a microneedle with an engaged implantable device may be referred to as a loaded or device-loaded microneedle. In some instances, useful microneedles include but are not limited to e.g., those microneedles fabricated according to the methods described herein. Methods, compositions and systems for device implantation that may find use in the subject methods of implanting a device into a tissue having an outer membrane may further include but are not limited to e.g., those described in PCT International Patent Application No. WO 2016/126340; the disclosure of which is incorporated herein by reference in its entirety.

The subject methods may find use in any method where a device is desired to be implanted into a tissue having an outer membrane, including those where the membrane may interfere with such implantation or it may be desirable to maintain the integrity of the membrane, including where e.g., the device includes but is not limited to a microneedle, an electrode, a waveguide, or the like. Non-limiting exemplary implantable devices are described below.

The size of the section of membrane ablated according to the described methods will vary. In some instances, the section of membrane ablated may correspond to the size of the implantable device to be inserted. For example, in some instances, the size of the hole made by ablation of the membrane may correspond with and allow for the insertion of an implantable device including e.g., those described below.

Implantable Devices

Subject implantable devices that can be implanted using the method of the present disclosure into a tissue having an outer membrane include e.g., a device that includes: (i) a biocompatible substrate (e.g., a non-conductive substrate, e.g., a flexible substrate such as a polyimide-based polymer), (ii) a conduit (e.g., a conductor of electricity such as an electrode, a conductor of photons such as a waveguide) that is disposed on the biocompatible substrate, and (iii) an engagement feature (e.g., a loop) for reversible engagement with an insertion needle. In some cases, the biocompatible substrate includes the engagement feature of the implantable device. In some cases, the conduit includes the engagement feature of the implantable device. A subject microneedle includes an engagement feature that corresponds to the engagement feature of the implantable device.

As used herein the term "conduit" refers to a substance that can conduct information to an external device. A conduit can be a conductor of electricity (e.g., an electrode), a conductor of photons (e.g., a waveguide such as an optic fiber), a conductor of fluid (e.g., a microfluidic channel), etc. As such, a subject implantable device can be used for a large variety of purposes, and this will depend on the nature of the conduit(s) present as part of the implantable device. For example, an implantable device can be used as (1) a sensor (detector), (2) an effector (e.g., to deliver a stimulation such as light, current, and/or a drug, e.g., which can change the tissue environment into which the device is implanted), or (3) both, depending on the nature of the conduit(s) present as part of the implantable device.

Examples of when a subject implantable device can be used as a sensor include, but are not limited to situations in which the device includes, as a conduit: (i) an electrode that is used as a recording electrode; (ii) a chemical sensing element such as an analyte sensor, e.g., a working electrode; (iii) a photodetector, e.g., for radiography and/or in-vivo imaging; etc.

Examples of when a subject implantable device can be used as an effector include, but are not limited to situations in which the device includes, as a conduit: (i) an electrode that is used for stimulation, e.g., for delivering a current; (ii) a light emitting diode (LED) and/or a microscale laser, e.g., for optogenetic applications; and/or (iii) a waveguide (e.g., optical fiber) for delivering light, e.g., for optogenetic applications; etc. In some cases, effectors will effect cells that have been physically, genetically, and/or virally modified to include (e.g., express) biological transducers (e.g., ion channels, RF-sensitive nanoparticles, and the like). For example, a subject implantable device that includes a waveguide (e.g., an optical fiber) may be used to irradiate and affect target naive or transfected tissue.

Because electrodes can be used as sensors (e.g., to detect changes in electrical activity) or as effectors (e.g., to deliver a current to the surrounding tissue), an implantable device that includes a conductor (e.g., an electrode) as a conduit can function in some cases as a sensor, as an effector, or as both. For example, electrodes can be used for closed and/or open-loop micro or macro stimulation.

As used herein the phrase "disposed on" (e.g., when a conduit is disposed on a biocompatible substrate) is meant to encompass cases in which the conduit is present on, within (e.g., sandwiched), or embedded within the biocompatible substrate. In some cases, the biocompatible substrate can provide mechanical shape/structure to the implantable device while the conduit can provide for communication with an external device. For example, a conduit (e.g., an electrode) can be sandwiched between substrate layers (e.g., non-conductive layers) and/or embedded within a biocompatible substrate, and such an element would be considered herein to be "disposed on" the biocompatible substrate (e.g., in some cases the biocompatible substrate can have more than one layer). In some cases, at least a portion of the conduit is exposed to the surrounding environment (e.g., when the conduit is an electrode).

The biocompatible substrate can be any convenient biocompatible substrate and in some cases will be an inert and non-conductive (e.g., insulating) biocompatible substrate (e.g., an insulator). In some cases, the biocompatible substrate is flexible (e.g., the biocompatible substrate is a flexible biocompatible substrate, e.g., a flexible biocompatible substrate, e.g., a flexible non-conductive biocompatible substrate). In some cases, the biocompatible substrate is inert. In some cases, the biocompatible substrate is inert and/or non-conductive.

A biocompatible substrate (e.g., a flexible biocompatible substrate) can be made from any convenient material. In some cases a biocompatible substrate (e.g., a flexible biocompatible substrate) comprises an inert polymeric material (e.g., polyimide, e.g., a polyimide-based polymer, parylene, etc.). In some cases a biocompatible substrate (e.g., a flexible biocompatible substrate) comprises polyimide (e.g., comprises a polyimide-based polymer). In some cases, the biocompatible substrate (e.g., a flexible biocompatible substrate) of a subject implantable device includes an inert polymeric material (e.g., polyimide, e.g., a polyimide-based polymer, parylene, etc.). In some cases, the biocompatible substrate of a subject implantable device includes a conductive material such as metal. In some cases, the biocompatible substrate of a subject implantable device includes NiTi (Nickel-Titanium).

For a non-conducting biocompatible substrate, any convenient non-conducting plastic or polymeric material and/or other non-conducting, flexible, deformable material can be used. Examples include but are not limited to thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate). In some cases, a dissolving polymer (e.g. polycaprolactone) can be used as an insertion shuttle. In some cases, a thin layer of dielectric (e.g., ceramic, glass, and the like) can be used as an insulator and barrier layer. In some cases, the first layer can be partially-cured (e.g., partially cured PI), in which case the stack can be PI-dielectric-metal-dielectric (e.g., PI-ceramic-metal-ceramic).

In some cases, a subject implantable device includes one or more insulating and/or moisture barrier layers (e.g., a dielectric, $Al_2O_3$, and the like). In some such cases, such layers might not be ductile (e.g., in some cases such a layer(s) is ductile and in some cases such a layer(s) is not ductile). In some cases, the biocompatible substrate is inert (e.g., can be an inert biocompatible substrate).

In some embodiments, a subject implantable device includes two layers of biocompatible substrate (e.g., non-conductive biocompatible substrate) with metal sandwiched within. In some cases, such an arrangement can provide, e.g., insulation in the inner layer and/or desirable mechanical properties in the outer layer. In some embodiments, a flexible biocompatible substrate of an implantable device includes first and second thin-film (e.g., of polyimide, of parylene, etc.) layers sandwiched around the conduit (e.g., metal). In other words, the conduit (e.g., metal) can be adjacent to the first thin-film (e.g., of polyimide, of parylene, etc.) layer; and the second thin-film (e.g., polyimide or parylene) layer, forming a thin-film metal thin-film sandwich.

A subject implantable device includes a conduit. Any convenient conduit can be used and a large variety of conduits are envisioned that would be useful in a large variety of settings, which can depend on context, e.g., what biological tissue is being targeted, what disease or condition is being treated, whether the implanted implantable device(s) will be used for research or therapeutic purposes, etc. Examples of suitable conduits include, but are not limited to: an electrode, a light emitting diode (LED) (e.g., for optogenetic applications), a microscale laser (e.g., for optogenetic applications), a chemical sensing element such as an analyte sensor/detector, a photodetector (e.g., for radiography or in-vivo imaging), an optical element such as a waveguide (e.g., an optical fiber), a reflectometry based sensor, and the like. In some cases, the conduit of a subject implantable device is an electrode. As noted above, in some cases an implantable device that includes an electrode can be used a sensor (detector), an effector (e.g., for stimulation of surrounding tissue), or both.

A conduit (e.g., an electrode for recording and/or stimulation) can comprise (e.g., can be made of) any convenient conductive material. For example, a conduit that conducts electricity (e.g., an electrode) can comprise: copper (Cu), titanium (Ti), copper and titanium, Nickel (Ni), Nickel-Titanium (NiTi, nitinol), chromium (Cr), platinum (Pt), platinum/iridium alloys, tantalum (Ta), niobium (Nb), zirconium (Zr), hafnium (Hf), Co—Cr—Ni alloys, stainless steel, gold (Au), a gold alloy, palladium (Pd), carbon (C), silver (Ag), a noble metal, an allotrope of any of the above, a biocompatible material, and any combination thereof.

In some embodiments, the conduit (e.g., electrode) of a subject implantable device comprises (e.g., is made of) a metalization stack selected from: Cr/Au, SiC/Pt, Pt/SiC, and Ta/Cr/Au. In some cases, the conduit (e.g., electrode) of a subject implantable device comprises Cr/Au (e.g., a Cr/Au metalization stack). In some cases, the conduit (e.g., electrode) of a subject implantable device comprises SiC/Ti/Pt/SiC (e.g., a SiC—Ti—Pt—SiC metalization stack). For example, SiC can be used for adhesion (e.g., as an adhesion layer, e.g., a 5-30 nm thick adhesion layer) to the biocompatible substrate (e.g., in some cases PI). of the subject implantable device while Ti can serve as an adhesion layer (e.g., a 5-30 nm thick adhesion layer) between Pt and SiC).

The conduit can have any convenient cross sectional shape, such as, but not limited to, a circular cross section, a rectangular cross section, a square cross section, a triangular cross section, a planar cross section, or an elliptical cross-section.

In some cases, a subject implantable device includes only one conduit (e.g., an electrode, a wave guide). In some cases, a subject implantable device includes one or more conduits (e.g., electrodes, waveguides) (e.g., two or more, three or more, four or more, five or more, six more, seven or more, eight or more, etc.). In some cases, a subject implantable device includes a plurality of conduits (e.g., electrodes, waveguides) (e.g., 2, 3, 4, 5, 6, 7, 8, 9, 10, 2 or more, 3 or more, 4 or more, 5 or more, 6 more, 7 or more, or 8 or more conduits). In some embodiments, when an implantable device includes more than one conduit (e.g., electrode), each conduit (e.g., electrode, waveguide) can be in communication (e.g., electrical communication, optic communication) with an external device, e.g., can be independently electrically connected to respective wires or fibers (e.g., such that electrical stimulation can be directed to selected electrodes and/or electrical activity can be detected by selected electrodes).

In some cases, a conduit of a subject implantable device is an electrochemical implantable device. An "electrochemical implantable device" is a device configured to detect the presence and/or measure the level of an analyte in a sample via electrochemical oxidation and reduction reactions on the implantable device. These reactions are transduced to an electrical signal that can be correlated to an amount, concentration, or level of an analyte in the sample. For more on using electrodes as an electrochemical implantable device, refer to U.S. Pat. No. 6,175,752, which is hereby incorporated by reference in its entirety.

For example, in some cases, a subject implantable device includes two or more electrodes where one electrode is a working electrode and another electrode is a counter electrode. In some cases, a subject implantable device includes two or more electrodes where one electrode is a working electrode and another electrode is a reference electrode. In some cases, a subject implantable device includes three or more electrodes where one electrode is a working electrode, one electrode is a counter electrode, and one electrode is a reference electrode.

A "counter electrode" refers to an electrode paired with the working electrode, through which passes a current equal in magnitude and opposite in sign to the current passing through the working electrode. The term "counter electrode" is meant to include counter electrodes which also function as reference electrodes (i.e., a counter/reference electrode). A "working electrode" is an electrode at which an analyte (or a second compound whose level depends on the level of the analyte) is electrooxidized or electroreduced with or without the agency of an electron transfer agent. An "electron transfer agent" is a compound that carries electrons between the analyte and the working electrode, either directly, or in cooperation with other electron transfer agents. One example of an electron transfer agent is a redox mediator. "Electrolysis" is the electrooxidation or electroreduction of a compound either directly at an electrode or via one or more electron transfer agents. A "working surface" is that portion of the working electrode which is coated with or is accessible to the electron transfer agent and configured for exposure to an analyte-containing fluid.

A variety of dimensions and geometries are suitable for a subject implantable device and any convenient set of dimensions/geometries can be used, and will likely vary based on various considerations such as, but not limited to: the type of target tissue, the type of conduit present (e.g., electrode, LED, laser, waveguide, etc.), the cost of materials, the rate and/or ease of fabrication, the level of desired tissue displacement, etc.

As used below, the term "maximum diameter" is used in the following context to mean the diameter of the implantable device at the point along its length at which it is its widest, and the term "maximum cross sectional area" is used to mean the cross sectional area of the implantable device at the point along its length at which the cross sectional area is greatest.

In some cases, the implantable device has a maximum diameter of 80 µm or less (e.g., 70µ or less, 65 µm or less, 60 µm or less, 55 µm or less, 50 µm or less, 55 µm or less, 50 µm or less, 45 µm or less, 40 µm or less, 35 µm or less, 30 µm or less, or 25 µm or less, 20 µm or less, 15 µm or less, 10 µm or less, 9 µm or less, 8 µm or less, 7 µm or less, 6 µm or less, 5 µm or less, 4 µm or less, 3 µm or less, 2 µm or less, 1 µm or less, 0.5 µm or less, etc.). For example, in some cases, the implantable device has a maximum diameter of 65 µm or less. In some cases, the implantable device has a maximum diameter of 35 µm or less. In some cases, the implantable device has a maximum diameter of 25 µm or less. In some cases, the implantable device has a maximum diameter of 15 µm or less. In some cases, the implantable device has a maximum diameter of 5 µm or less.

In some cases, the implantable device has a maximum diameter in a range of from 0.5 to 80 µm (e.g., from 0.5 to 70 µm, from 0.5 to 65 µm, from 0.5 to 60 µm, from 0.5 to 55 µm, from 0.5 to 50 µm, from 0.5 to 45 µm, from 0.5 to 40 µm, from 0.5 to 35 µm, from 0.5 to 25 µm, from 0.5 to 15 µm, from 0.5 to 5 µm, from 15 to 80 µm from 15 to 70 µm, from 15 to 65 µm, from 15 to 60 µm, from 15 to 55 µm, from 15 to 50 µm, from 15 to 45 µm, from 15 to 40 µm, from 15 to 35 µm, from 20 to 80 µm from 20 to 70 µm, from 20 to 65 µm, from 20 to 60 µm, from 20 to 55 µm, from 20 to 50 µm, from 20 to 45 µm, from 20 to 40 µm, from 20 to 35 µm, from 25 to 80 µm from 25 to 70 µm, from 25 to 65 µm, from 25 to 60 µm, from 25 to 55 µm, from 25 to 50 µm, from 25 to 45 µm, from 25 to 40 µm, or from 25 to 35 µm). In some cases, the implantable device has a maximum diameter in a range of from 0.5 to 65 µm. In some cases, the implantable device has a maximum diameter in a range of from 10 to 65 µm. In some cases, the implantable device has a maximum diameter in a range of from 0.5 to 35 µm. In some cases, the implantable device has a maximum diameter in a range of from 10 to 35 µm.

In some cases, the implantable device has a maximum cross sectional area of 5000 µm² or less (e.g., 4500 µm² or less, 4000 µm² or less, 3500 µm² or less, 3000 µm² or less, 2500 µm² or less, 2000 µm² or less, 1500 µm² or less, 1000 µm² or less, 800 µm² or less, 750 µm² or less, or 700 µm² or less, or 600 µm² or less, or 500 µm² or less, or 400 µm² or less, or 300 µm² or less, or 250 µm² or less, or 200 µm² or less, or 150 µm² or less, or 100 µm² or less, or 90 µm² or less, or 80 µm² or less, or 70 µm² or less, or 60 µm² or less, or 50 µm² or less, or 40 µm² or less, or 30 µm² or less, or 20 µm² or less, or 10 µm² or less, etc.). In some cases, the implantable device has a maximum cross sectional area of 1000 µm² or less (e.g., 900 µm² or less, 800 µm² or less, 700 µm² or less, 600 µm² or less, 500 µm² or less, 400 µm² or less, 300 µm² or less, 200 µm² or less, or 100 µm² or less, etc.). In some cases, the implantable device has a maximum cross sectional area of 100 µm² or less (e.g., 90 µm² or less, 80 µm² or less, 70 µm² or less, 60 µm² or less, 50 µm² or less, 40 µm² or less, 30 µm² or less, or 20 µm² or less).

In some cases, the implantable device has a maximum cross sectional area in a range of from 2.5 to 4000 µm² (e.g., from 2.5 to 3500 µm², from 2.5 to 3000 µm², from 2.5 to 2500 µm², from 2.5 to 3000 µm², from 2.5 to 2500 µm², from 2.5 to 2000 µm², from 2.5 to 1500 µm², from 2.5 to 1000 µm², from 2.5 to 500 µm², from 2.5 to 250 µm², from 2.5 to 100 µm², from 2.5 to 50 µm², from 2.5 to 10 µm², from 10 to 4000 µm², from 10 to 3500 µm², from 10 to 3000 µm², from 10 to 2500 µm², from 10 to 3000 µm², from 10 to 2500 µm², from 10 to 2000 µm², from 10 to 1500 µm², from 10 to 1000 µm², from 10 to 500 µm², from 10 to 250 µm², from 10 to 100 µm², from 10 to 50 µm², from 10 to 25 µm², from 100 to 4000 µm², from 100 to 3500 µm², from 100 to 3000 µm², from 100 to 2500 µm², from 100 to 3000 µm², from 100 to 2500 µm², from 100 to 2000 µm², from 100 to 1500 µm², from 100 to 1000 µm², from 500 to 4000 µm², from 500 to 3500 µm², from 500 to 3000 µm², from 500 to 2500 µm², from 500 to 3000 µm², from 500 to 2500 µm², from 500 to 2000 µm², from 500 to 1500 µm², from 500 to 1000 µm², from 500 to 800 µm² from 1000 to 4000 µm², from 1000 to 3500 µm², from 1000 to 3000 µm², from 1000 to 2500 µm², from 1000 to 3000 µm², from 1000 to 2500 µm², from 1000 to 2000 µm², from 1000 to 1500 µm², from 2000 to 4000 µm², from 2000 to 3500 µm², from 2000 to 3000 µm², from 2000 to 2500 µm², from 2000 to 3000 µm², from 2000 to 2500 µm², from 2500 to 4000 µm², from 2500 to 3500 µm², from 2500 to 3000 µm², from 2500 to 2500 µm², or from 2500 to 3000 µm²).

In some cases, the implantable device has a maximum cross sectional area in a range of from 2.5 to 1000 µm². In some cases, the implantable device has a maximum cross sectional area in a range of from 2000 to 4500 µm². In some cases, the implantable device has a maximum cross sectional area in a range of from 5 to 100 µm². In some cases, the implantable device has a maximum cross sectional area in a range of from 100 to 1000 µm². Implantable devices, such as implantable probes, may be of essentially any dimension including those falling within the maximum dimensions described above. In some cases, an implantable device may be dimensioned from 0.5 µm to 100 µm by 5 µm to 1000 µm, including e.g., 0.5 µm by 1000 µm, 0.5 µm by 750 µm, 0.5 µm by 500 µm, 0.5 µm by 250 µm, 0.5 µm by 100 µm, 0.5 µm by 75 µm, 0.5 µm by 50 µm, 0.5 µm by 25 µm, 0.5 µm by 10 µm, 0.5 µm by 5 µm, 1 µm by 1000 µm, 1 µm by 750 µm, 1 µm by 500 µm, 1 µm by 250 µm, 1 µm by 100 µm, 1 µm by 75 µm, 1 µm by 50 µm, 1 µm by 25 µm, 1 µm by 10 µm, etc.

Devices and Kits

Also provided are devices and kits thereof for practicing one or more of the above-described methods. For example, devices including e.g., devices for use in fabricating microneedles according to the methods described herein are included. Such devices will vary any may include but are not limited to e.g., devices that include components for holding lengths of wire in place and/or winding wires (such as e.g., a winding jig), devices that include components for brazing wound wire (such as, e.g., a brazing machine), and the like. Devices for insertion of an implantable device into a biological tissue having an outer membrane are also included. Such devices will vary and may include but are not limited to e.g., an ablation laser, a targeting and implantation rig that includes an ablation laser, and the like. Also included are kits for practicing the subject methods including e.g., kits for fabricating microneedles that include e.g., components of the methods described above including but not limited to e.g., wires, brazing material, one or more of the above described devices, etc. Also included are kits for implanting an implantable device into a tissue having an outer membrane that include components of the above described methods including e.g., one or more photosensitizers, one or more implantable devices, a microneedle, components for microneedle fabrication, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Microneedle Fabrication

Methods involving the insertion of an implantable device into a biological tissue may involve using a microneedle with a reversible engagement feature to implant the implantable device and subsequently retract the microneedle leaving the implantable device implanted in the biological tissue as a desired location.

One implemented design of a microneedle (100) having a reversible engagement feature (101) with implantable device (102) engaged is depicted in FIG. 1. Here two wires are twisted together to from the microneedle and one wire is made longer, by 100-150 µm, and one shorter. The longer wire is sharpened via electrochemical etching, while the shorter is blunt. These needles are often too fine (composed of wires <15 µm in diameter) to support themselves without buckling outside of a small cannula (70 µm or less ID), hence may be fabricated to be thicker along a length, particularly along the portion that resides within a telescoping section of cannula to provide support and prevent buckling. A photograph of the microneedle schematized FIG. 1, loaded into a cartridge, showing the step engagement feature and the sharpened point at the bottom is provided in FIG. 2.

Figure 3B:
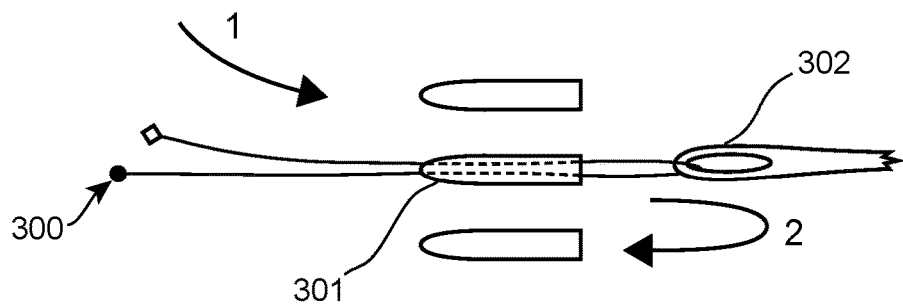
Figure 3C:
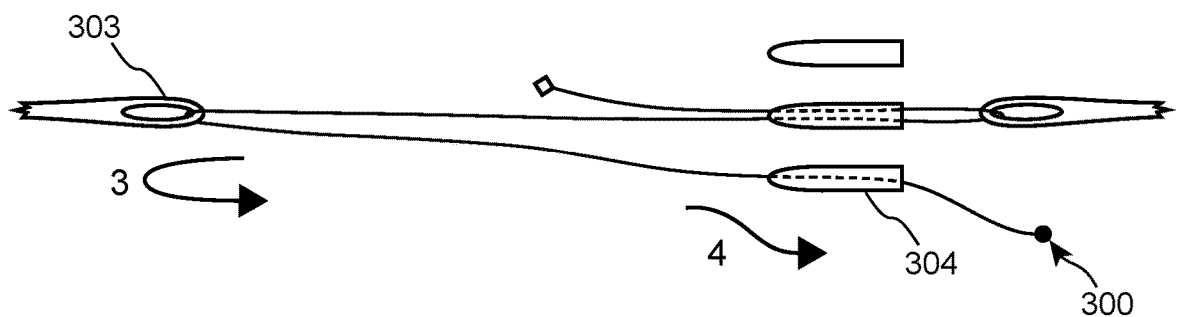
Figure 3D:
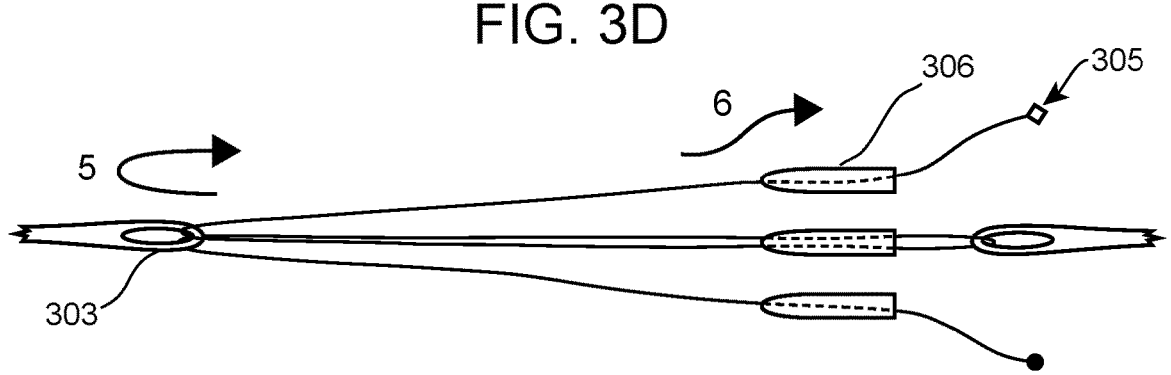

In the instant example of microneedle fabrication, a length of fine (5-50 µm) tungsten, tungsten-rhenium, carbon, or other stiff, strong, high-melting point materials and alloys thereof is wound in a "W" shape on a winding jig, e.g., as schematically depicted in FIG. 3A. A step-by-step process of loading the winding jig is depicted in FIGS. 3B-3D. Specifically, the wire is wound on the winding jig by maneuvering one end (closed circle, 300) through the middle eyelet (301), the first loop (302) and back through the middle eyelet again (FIG. 3A). Next, the end (closed circle, 300) is passed through the second loop (303) and the bottom eyelet (304) (FIG. 3C). Next, the other end (open rhombus, 305) is passed through the second loop (303) and back through the top eyelet (306) (FIG. 3D). Both ends are tightened under clamps and tension is maintained in the four strands.

Figure 4:
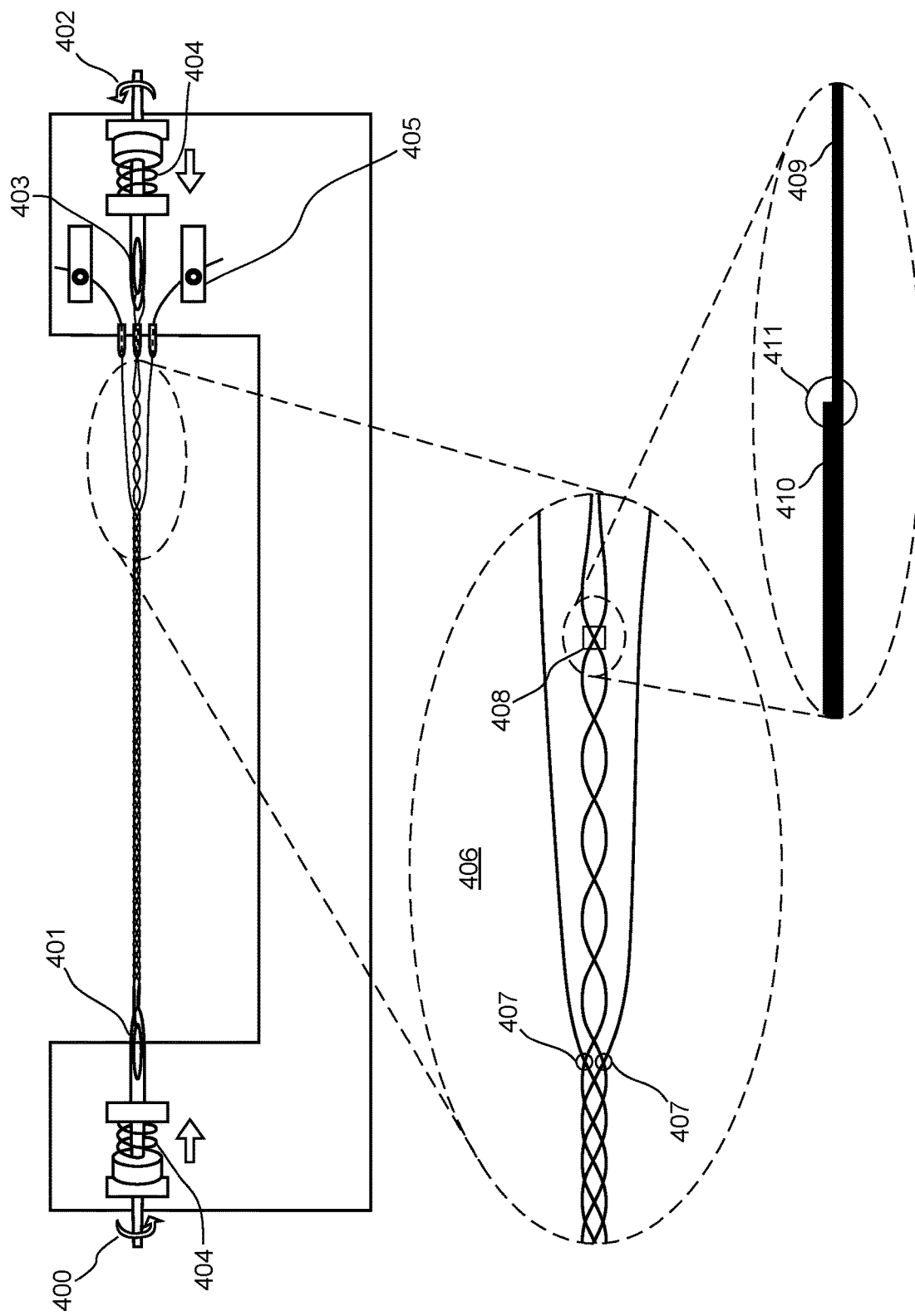
FIG. 4 provides a schematic representation of wire winding and the associated fracture points in the wound wire according to an embodiment as described herein.

As depicted in FIG. 4, once the tungsten wire is loaded in the jig all four strands are twisted 70 times by rotating the left wheel (400), which is mounted with the second loop (401). Then two inner strands are twisted 10 times by rotating the right wheel (402), which is associated with the first loop (403). While rotating, the tungsten wire pulls the first and second loop holders inward, and the springs (404) mounted on the jig maintain tension on the wire strands. The spring elements tension the wires equally and clamp elements (405) hold the wire ends one tension has been established. One end of the "W" is a loop which the wire runs through twice; this loop free to turn, thereby allowing all 4 wires to be twisted into a helix. The other end, through which only one pass-through of wire, is also of a loop that's free to turn, and allows the 2 wires to form a continuation of the 4-helix. Thus, two wires (the ends) break off from the helix 1-30 mm before the end loop, while the 2 that continue have the same helix angle. Given the helices generated at the end nearest the first loop (406), following brazing with copper-iridium as described below, the two ends of the outer strands are removed at the indicated outer-strand break points (407) and one of the inter strands is removed at the indicated inner-strand break point (408). The unbroken inner strand serves as the microneedle tip (409) the end of the broken inner strand (410) provides an engagement feature (411).

Figure 5:
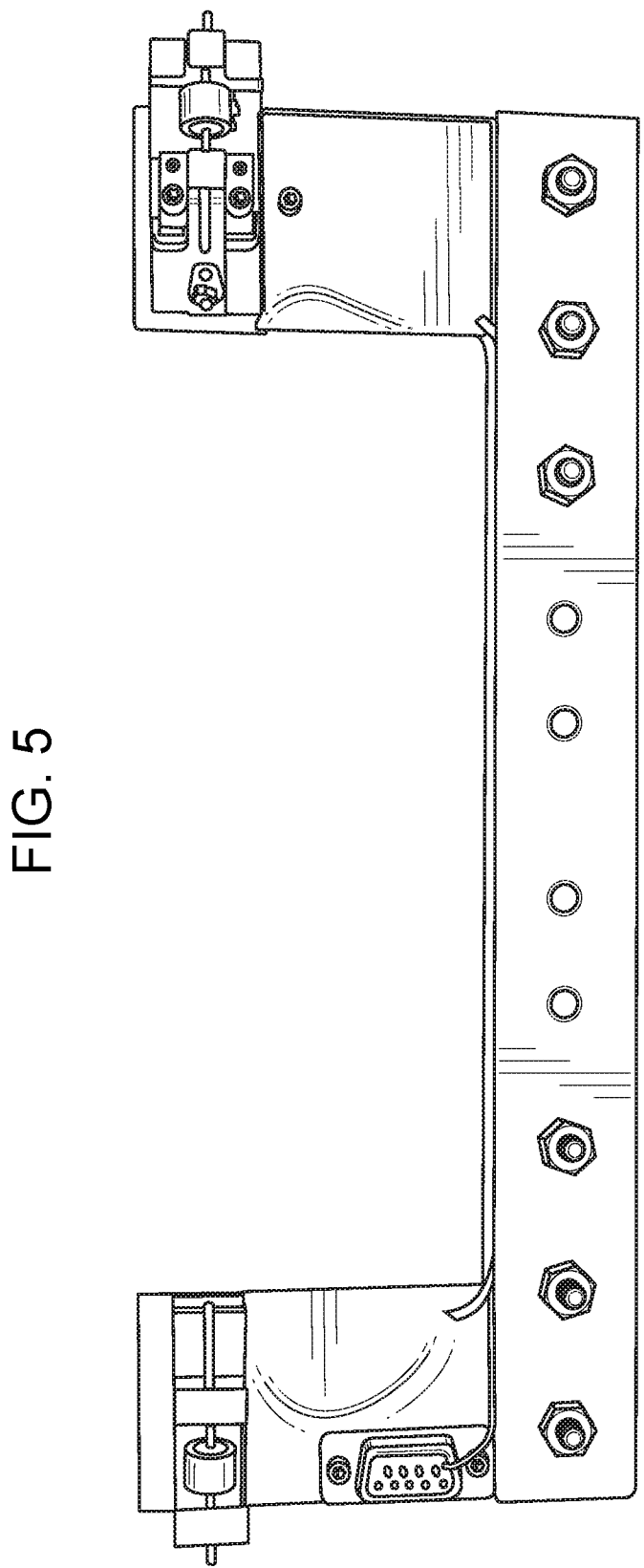
FIG. 5 provides a photo of a needle brazing jig, with wire visible, prior to brazing as described herein.
Figure 6:
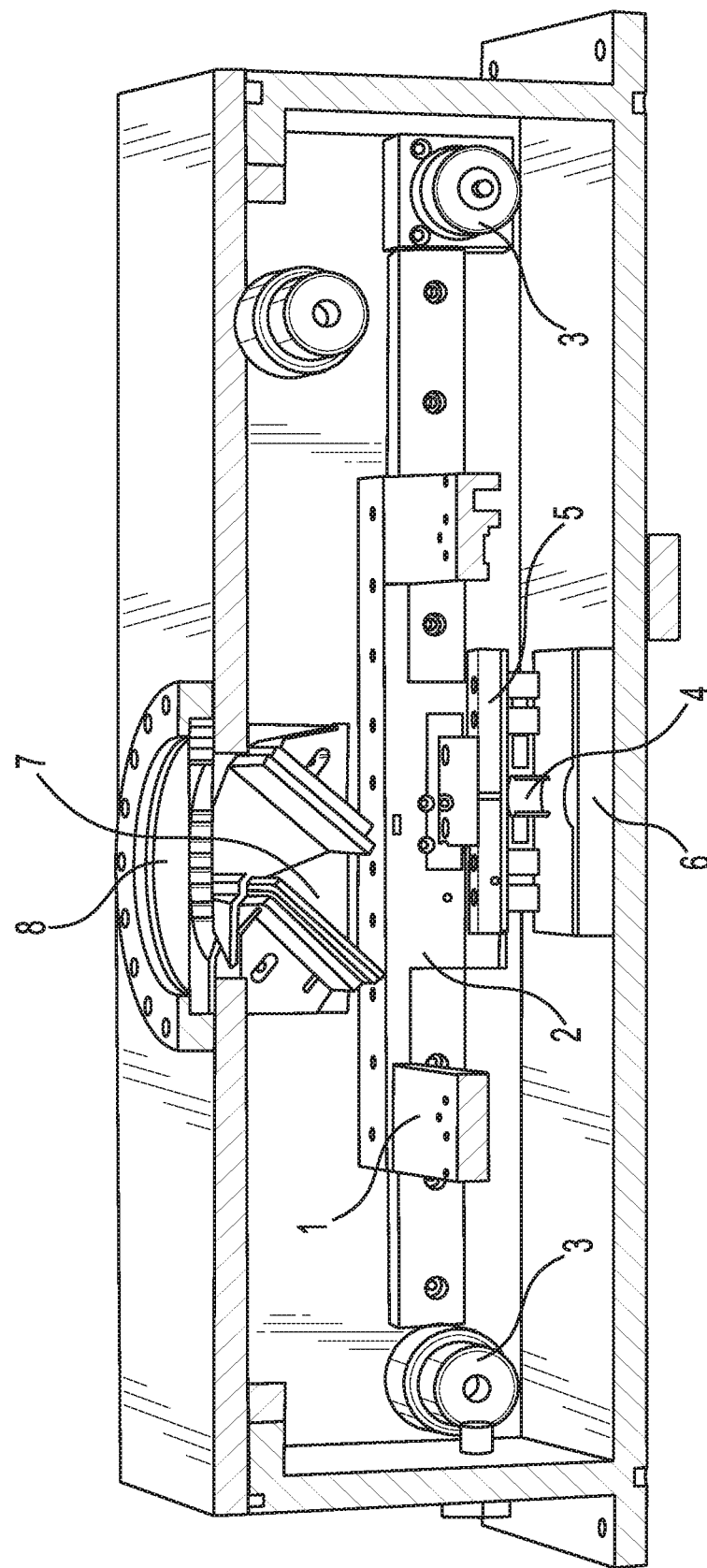
FIG. 6 provides a cross-sectional rendering through an embodiment of a needle brazing machine as described herein.
Figure 7:
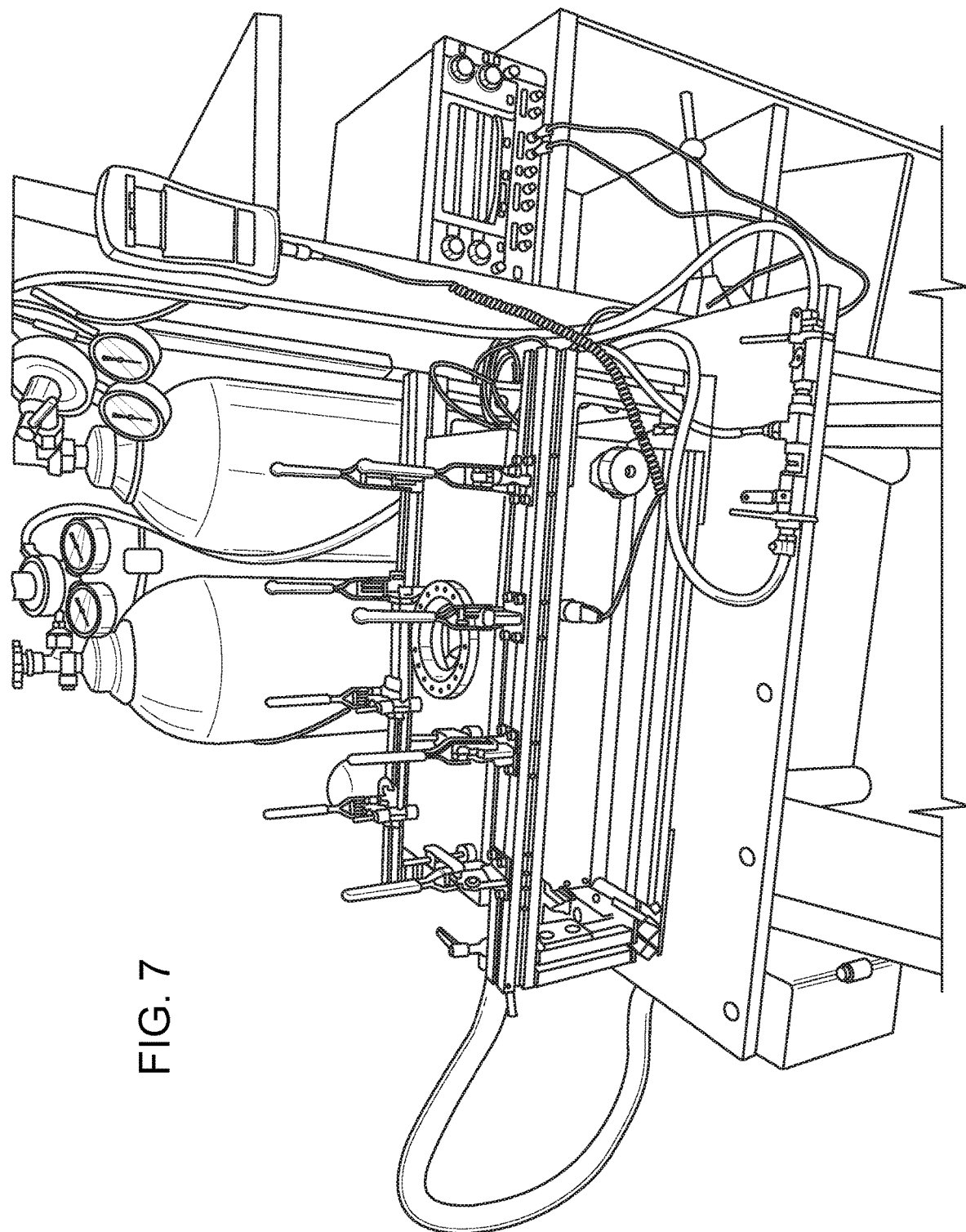
FIG. 7 provides a photograph of the assembled, working needle brazing machine chamber as described herein.
Figure 8:
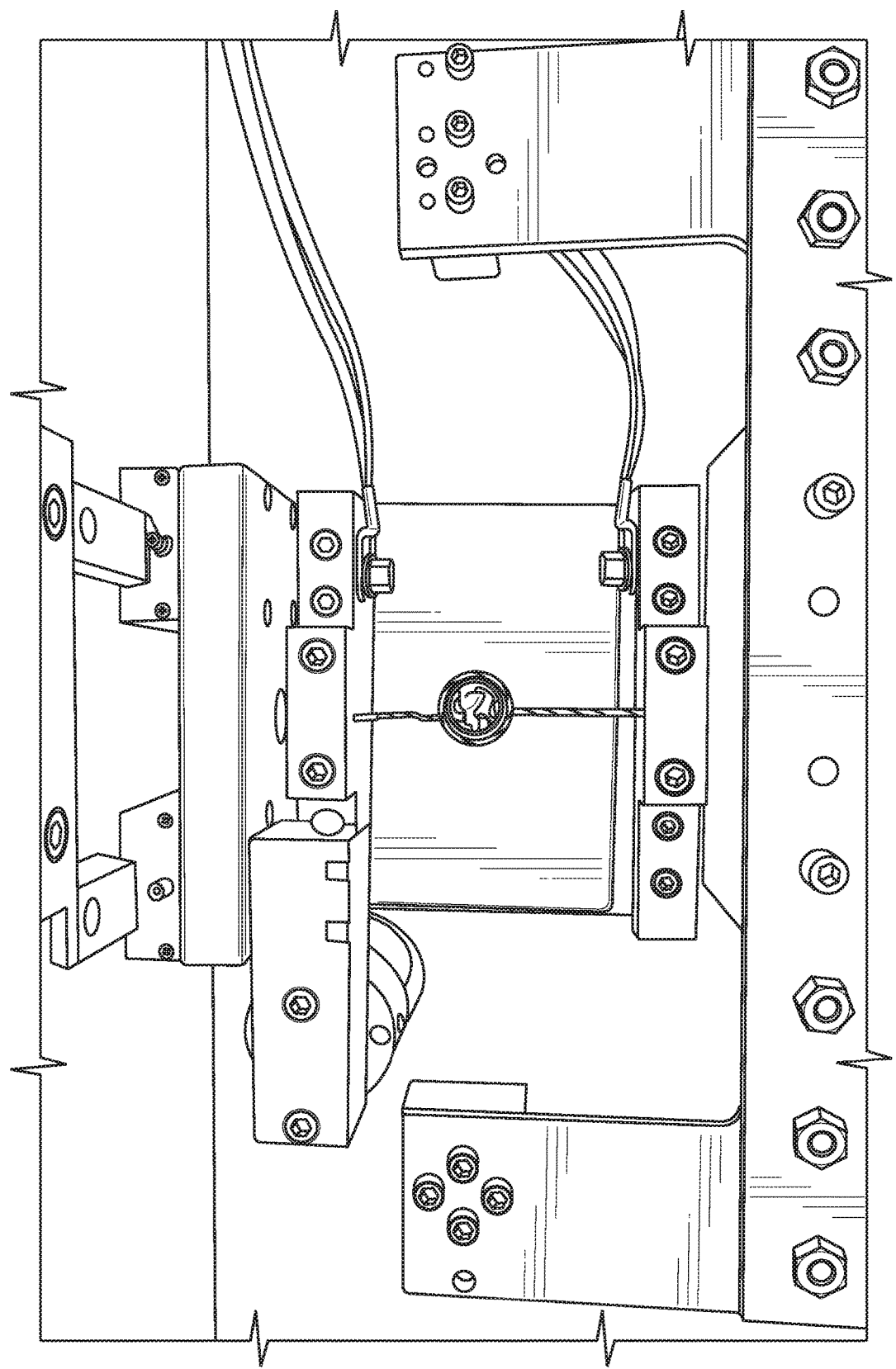
FIG. 8 provides a photograph of the interior of the brazing machine, with the copper melt and needle jig installed as described herein.

This needle winding jig has the added feature that the two ends are electrically isolated. For brazing, the needle winding jig with needle loaded (which may be referred to as a brazing jig) is then installed in a chamber. A photo of the needle brazing jig, with wire loaded prior to brazing is provided in FIG. 5. On the left, visible in FIG. 5, is a connector for supplying current to heat the needle for surface oxide reduction and recrystallization. A schematic cross-sectional rendering of the brazing chamber is provided in FIG. 6. Specifically FIG. 6 shows the jig (1) installed on a linear slide (2), which moves laterally under control of a pulley system (3) attached to the end of vacuum feedthroughs. The melt (4) is held in a tungsten heater basket, in turn mounted to heavy current busses (5) (in turn fed by vacuum feed-throughs) which are mounted on a base which can move vertically (6). This permits the user to dip the wire into the melt under visual control through the viewing maze (7), which prevents copper from condensing on the viewing window (8) in the lid. Photos of the brazing chamber and the melt within the chamber are provided in FIG. 7 and FIG. 8, respectively.

During brazing, the chamber is brought down to a vacuum of <10 mTorr, before a shielding gas is flowed through, a mixture of very dry argon and hydrogen (in practice 20% $H_2$ in Ar at a pressure of 500-600 mTorr). This gas mixture is continuously pumped out, so any water vapor produced is rapidly removed. It has been found that the pressure ratio of $H_2:H_2O$ should be sufficiently high to reduce any surface oxides on the most oxidizable surface, usually tungsten, at the braze and recrystallization temperatures, as estimated via an Ellingham diagram.

Then, bias current is passed through the needle wires until they are >1000 C, at which point the oxides on the surface of the wire are reduced (or sublimate), leaving a clean metal surface. This temperature can be, and usually is, further adjusted to recrystallize the wire, which facilitates the generation of the engagement feature. This temperature is currently measured by examining the color of the wire by eye through the viewing port, but could also be measured by an optical pyrometer or via resistance changes of the underlying wire or other means. The recrystallization step has an added feature that, due to reduced emission area and non-linear dependence of resistance on temperature, only the helix gets above the critical temperature, leaving the free ends (effectively those after the break-away points) in the ductile state; this makes fatiguing and handling the free ends considerably easier, and biases the break point close to the helix. Following bias recrystallization a mass of element/alloy immiscible with the wire material above the liquidus temperature, (in this example copper in a carbon or boronnitride (BN) crucible), is brought significantly above its melting temperature, and raised to meet the wire. Copper has a very high contact angle with carbon and BN, which means that the meniscus of molten copper can significantly exceed the lip of the crucible, facilitating this step. The carbon crucible also serves to scavenge any available $O_2$ in the system, which is desirable. In a carbon crucible dangerous tungsten carbide can form on the bare tungsten, using a boron-nitride crucible circumvents this issue and allows the use of carbide-forming elements in the braze alloy. The needle-winding jig is then smoothly moved laterally several times at approximately 1 cm/s by use of the pulley system identified in FIG. 6, such that the molten braze metal joins the multiple wires into a single part.

Pure Cu and Cu—Ir alloy have been repeatedly tested and found to be sufficient for needle brazing. However, as described in detail above, other elements/alloys may be employed.

The nascent needle is then removed from the molten braze material, the heating elements to the crucible are disengaged, and the vacuum chamber is allowed to cool prior being flushed with argon or another inert gas. At this point, it is possible and advisable to pass current to heat the needle to a tempering temperature of about 500° C., for a period of about 30 minutes to improve the strength and modulus of the braze. The chamber is then opened, and the needle-winding jig is removed. Then, three of the four wires that exit the helix are removed by fatiguing the wire, at the points at the points described above. Two of the constituent wires exit the helix 1-30 mm from the last, and provide strength to prevent buckling within the telescoping cannula.

The annealing/reducing temperature significantly influences the wire characteristics which in turn influence the fracture at the engagement feature. It was found that when a lower annealing/reducing temperature was employed the wire retains its ductile nature leading to a barb shaped, rather than a step shaped, engagement feature. It was also found that when a higher annealing/reducing temperature was employed the entire needle is considerably more brittle. This increase in overall brittle character of the needle leads to needles that are likely to fracture during assembly and during use. As-drawn, the wire has very elongated crystalline domains, which leads to ductility and high tensile strength of the material; these domains become more regular, and orient perpendicular to the direction of applied stress (tension due to springs in the needle-winding jig) during annealing and recrystallization. The addition of rhenium to the tungsten wire provides two advantages at this point: it raises the recrystallization temperature, so that the window between surface-oxide reduction and recrystallization is larger, and it increases the strength and modulus of the resulting needle. The quality and angle of the engagement features are affected by the recrystallization temperature that the wire is subjected to before being dipped in the copper (Cu) melt. Successful fabrication of a microneedle with desired characteristics has been empirically verified using recrystallization temperatures of about 1300° C. for pure tungsten (W) wire, and 1600° C. for tungsten-rhenium (W-26% Re) wire.

In instances where the shorter wire tends to break near (e.g., about 10 μm) where the braze fillet ends, leading to a "fork" which thin electrodes can be stuck in during insertion, very fine sandpaper (e.g., 10 μm grit) may be employed to remedy this situation. In such instances, the very fine sandpaper is delicately run along the needle, with three wires removed, but one wire still attached to the needle-winding jig, until the final step is eroded to the point that no fork can be observed, and the needle is essentially as drawn in the above figures.

Figure 9:
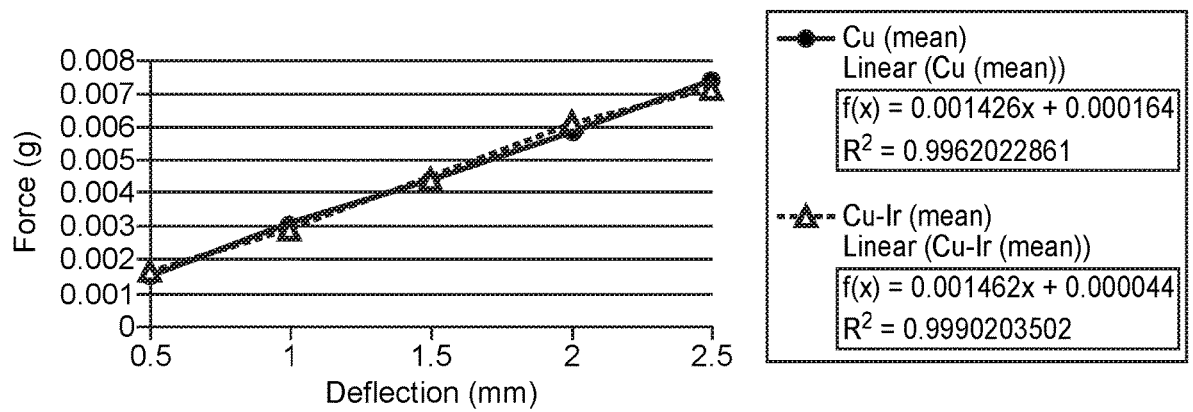
FIG. 9 provides measurements of needle elastic modulus, using a 1 cm extended segment pushing on a weigh-paper wedge on an analytic balance, for varying lateral displacements. The analyzed needle segment, fabricated according to one embodiment of the present disclosure, was of 4 wires throughout the 1 cm length. Modulus improvement was observed with iridium (Ir) addition; braze was not tempered. Overall modulus was measured to be close to that of bulk tungsten (W), 411 GPa.

Youngs modulus has been measured for both Cu and Cu—Ir brazed needles to be 379 GPa and 383 GPa, respectively, with an accurate model of the area moment of inertia for the 4 wire cross-section. Data for force vs deflection is shown in FIG. 9.

Figure 10:
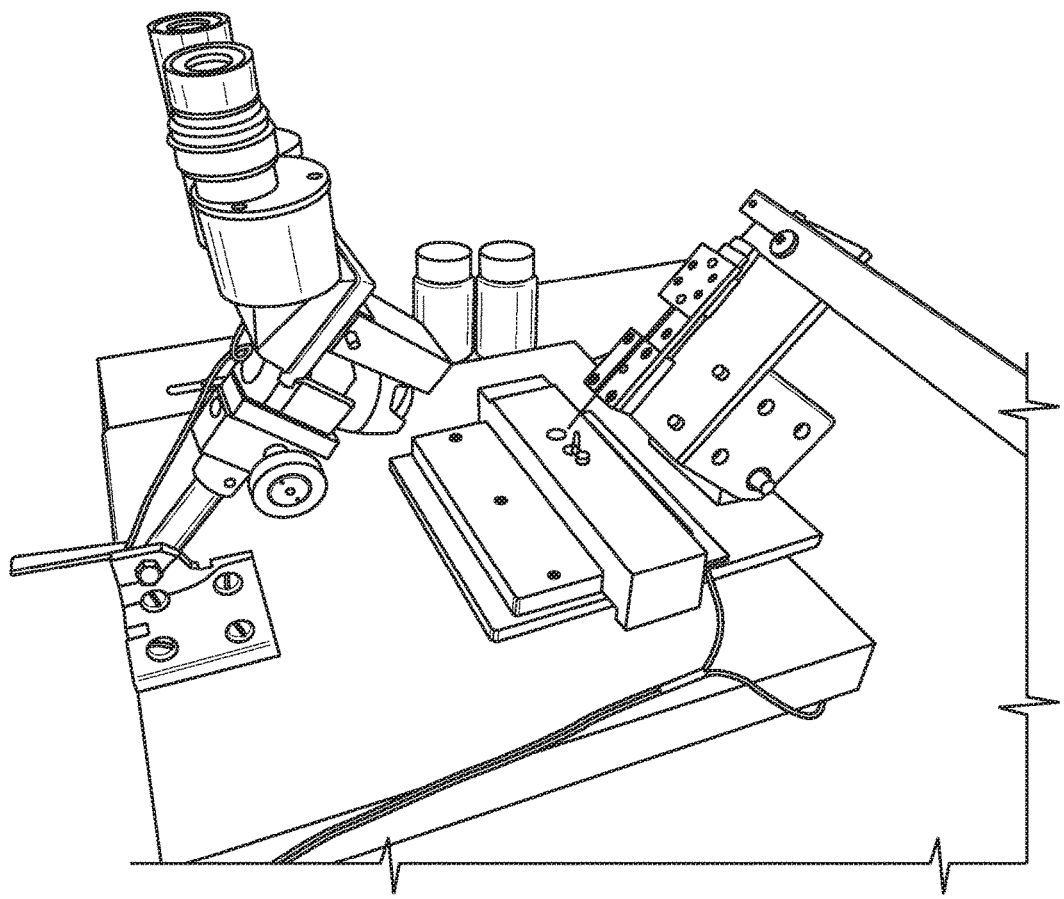
FIG. 10 provides a photograph of a needle etching and inspection station suitable for use in the methods as described herein.

At this point, the needle is loaded into a quadruple-telescoping cartridge, the far end is attached to the upper part of this cartridge, and this device is installed in another machine for inspecting and etching the needle, shown in FIG. 10. This machine consists of a microscope and two etchant wells. The first etchant well is $FeCl_3$, for removing Cu from the surface of the needle; the microscope is used to dip the needle into the solution just to the point of the shoulder/final break. The second is 1M NaOH, which is used with 1-6V AC to electrolytically etch the longest part of the needle to an extremely fine point. This machine also affords assessment of needle motion, which can be impeded if any dust entered the cannula during assembly.

Alternative Brazing Processes

An alternative brazing process has been tested. This alternative process involves the use of elements in the braze that bring tungsten into solution and thereby alloy substantially with this base metal. In this scheme, a copper or gold base (solvent) is used to dissolve to saturation Ni, Cr, Fe, or Co. These stay in solution until the wire, heated by laser or resistance, evaporates away the copper, and the Ni/Fe/Cr/Co is sufficiently above liquidus temperature to alloy directly with the W. The alloying will increase the liquidus temperature, stopping the wire from completely going into solution, and if properly controlled results in a strong, stiff bond.

A second example of this process is to evaporate or sputter a controlled quantity of alloying element on the surface of a tungsten-rhenium (W/W—Re) wire. This surface coating is then melted via laser, alloying with the W, and forms the desired fillet with the wires.

It has been found that in either of these approaches the quantity of element that directly alloys with W should be kept insufficient to penetrate the bulk of the wire. Where such quantity is not kept insufficient, the element may penetrate the bulk of the wire causing it to break under the tension of the winding jig.

Example 2

Laser Micro-Drilling

The needle as fabricated as describe herein is generally so fine and small that, in certain applications, when loaded with an electrode, it may not be able to reliably penetrate a desired biological tissue. For example, it was found that needle as fabricated as describe herein may fail to reliably penetrate rat dura, buckling in approximately 1 out of 10 insertions. In some instances as well, when an electrode/needle combination does penetrate a desired biological tissue (e.g., rat dura) it may pull a significant mass of surface material (e.g., collagen/elastin from the fibrous meningeal tissue) along with it. This situation may cause the electrode to adhere to the needle sufficiently tightly such that approximately one out of two inserted electrodes are removed with the needle, even when ballistic retraction is employed.

It was found that rat dura is approximately the same thickness/toughness as the non-human primate (NHP) pia-arachnoid complex (PAC). PAC, whether rat or NHP, is not easily dissected away. Durotomy in the rat, although not necessarily required to insert electrodes, can be avoided by employing the following methods thereby reducing trauma to the brain and improving surgical outcomes.

To remedy both these issues and provide other benefits (e.g., to give allow for further reducing the needle and/or electrode size), a system for laser-drilling micro-holes (e.g., in the dura (rat) or PAC (NHP)) has been developed and integrated into implantation procedures.

Figure 11:
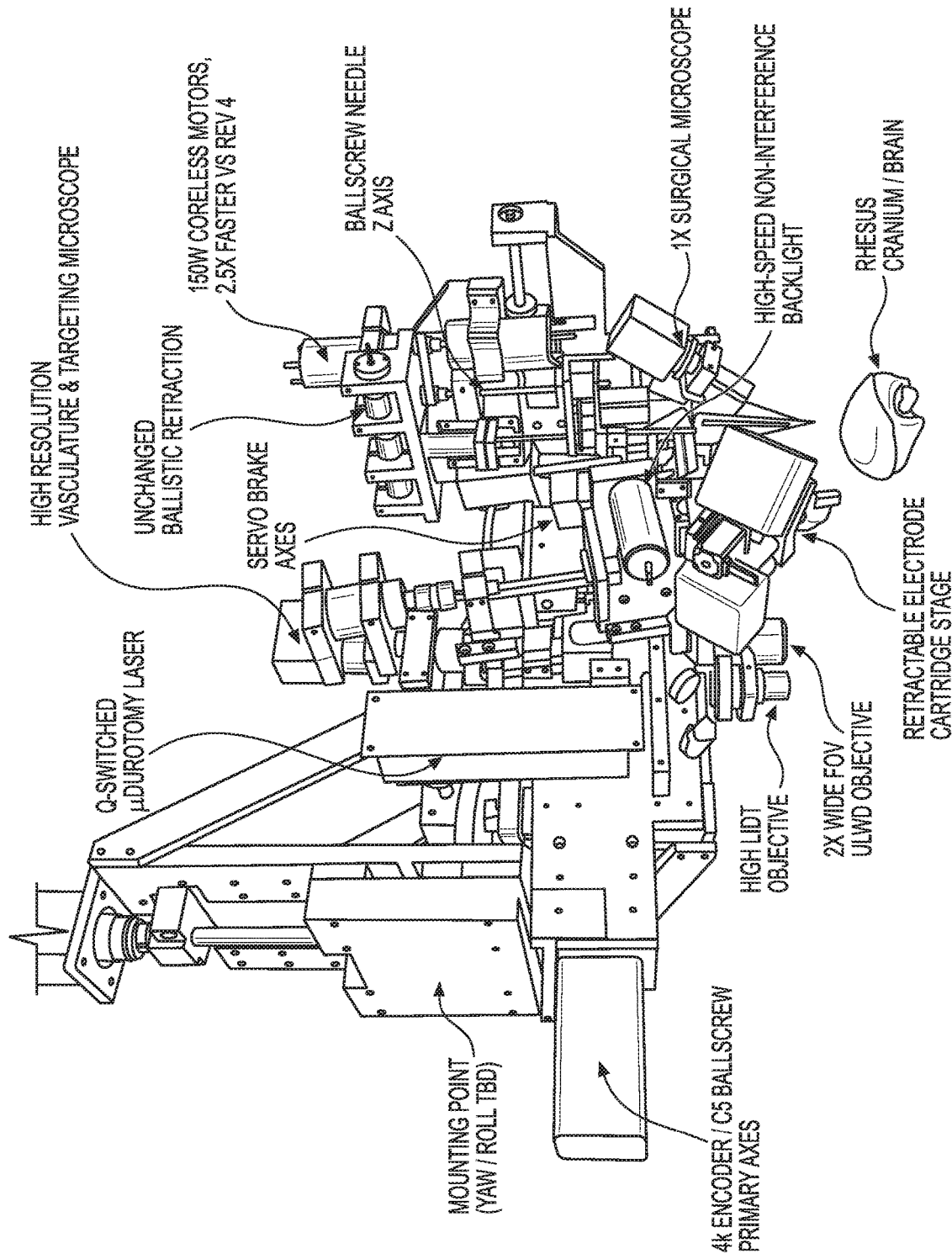
FIG. 11 provides an annotated rendering of an embodiment of an implantation system (also referred to as an inserter robot), showing, among other components, the imaging and laser-drilling optical heads.
Figure 12:
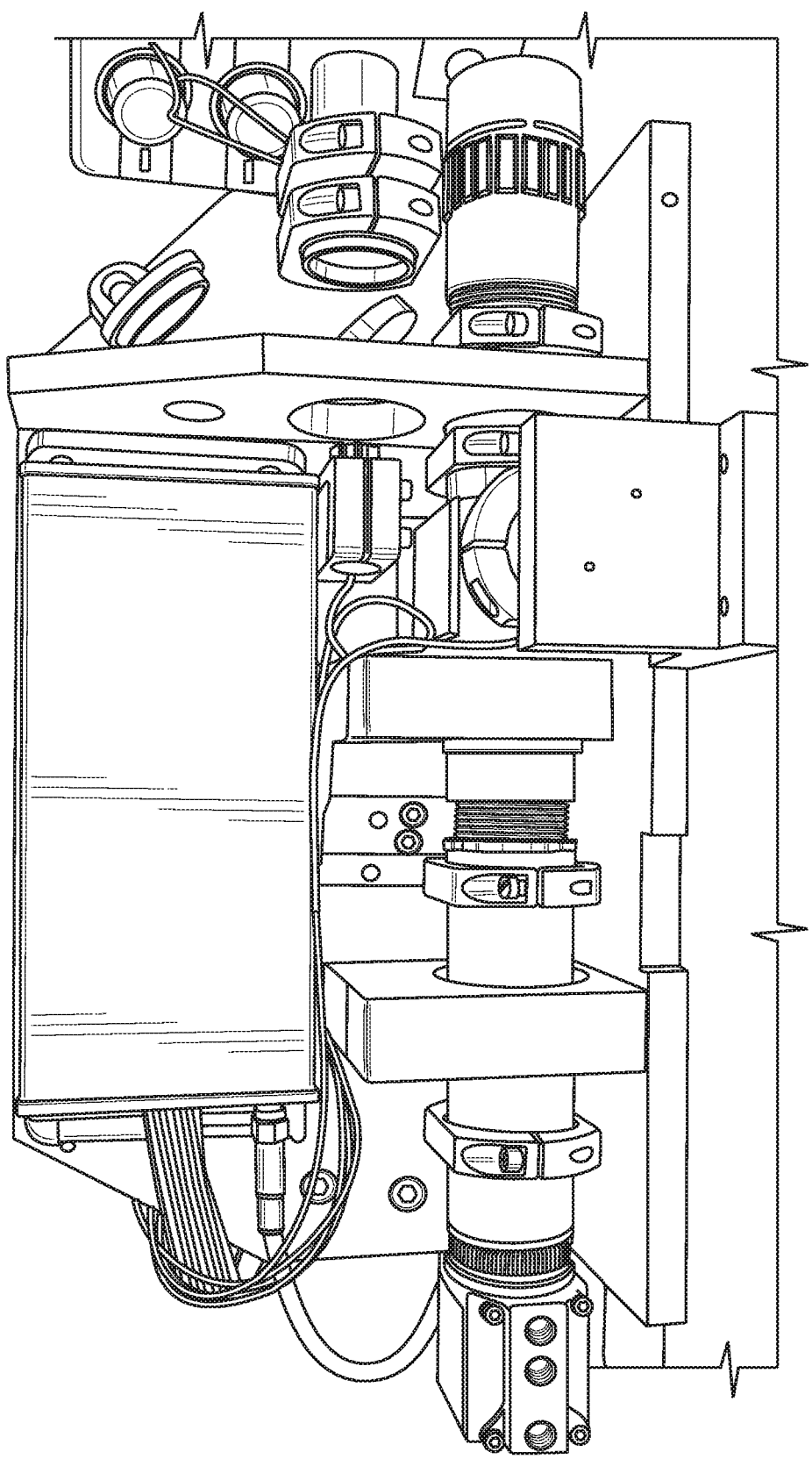
FIG. 12 provides a photograph of an assembled and tested optical stage component of one embodiment of the integrated implantation device. In the photograph the 527 nm drilling laser is active.

Specifically, in the instant example a q-switched green (527 nm) laser was employed for drilling micro-holes in dura and PAC dyed with Erythrosin B, a food-grade dye with a strong absorption peak at the emission wavelength. Unlike typical laser surgery approaches, here a non-ionizing wavelength was employed which is weakly absorbed by the tissue. Thus, when diffusion of the dye is controlled, off-target damage can also be controlled and minimized. This approach also makes possible the use of a ionizing (e.g. UV) Q-switched or pulsed laser to ablate the tissue without heating or cautery effect. A schematic image of the system employing this micro-hole laser drilling approach is provided in FIG. 11 and a photo of the working laser drilling, removed from the integrated system, is shown in the photograph provided in FIG. 12.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of inserting an implantable device into a biological tissue comprising an outer membrane, the method comprising:
   contacting an area of the outer membrane with a photosensitizer having a wavelength of strong absorption;
   ablating a section of the outer membrane by applying, to the area or a portion thereof, a laser with an emission wavelength that corresponds to the wavelength of strong absorption of the photosensitizer; and
   inserting the implantable device into the biological tissue through the ablated section of the outer membrane.

2. The method according to claim 1, wherein the emission wavelength is a non-ionizing emission wavelength.

3. The method according to claim 1, wherein the laser is a q switched laser.

4. The method according to claim 1, wherein the photosensitizer is a dye.

5. The method according to claim 4, wherein the dye comprises erythrosin B.

6. The method according to claim 1, wherein the biological tissue comprises central nervous system (CNS) tissue.

7. The method according to claim 6, wherein the CNS tissue comprises brain tissue.

8. The method according to claim 6, wherein the CNS tissue comprises spinal cord tissue.

9. The method according to claim 1, wherein the outer membrane comprises dura.

10. The method according to claim 1, wherein the outer membrane comprises pia-arachnoid complex.

11. The method according to claim 1, wherein the biological tissue is present in a live mammal.

12. The method according to claim 11, wherein the live mammal is a rodent.

13. The method according to claim 11, wherein the live mammal is a non-human primate.

14. The method according to claim 1, wherein the implantable device comprises a biocompatible substrate and a conduit disposed on the biocompatible substrate.

15. The method according to claim 14, wherein the conduit is a conductor of electrons and is an electrode for stimulating or recording.

16. The method according to claim 14, wherein the conduit is a waveguide.

17. The method according to claim 14, wherein the implantable device comprises two or more conduits.

18. The method according to claim 17, wherein the two or more conduits include two or more electrodes.

19. The method according to claim 1, wherein the implantable device is inserted into the biological tissue using a microneedle loaded with the implantable device.

20. The method according to claim 19, wherein the method further comprises retracting the microneedle to allow the implantable device to remain implanted in the biological tissue.

* * * * *